(12) United States Patent
Rivet-Sabourin et al.

(10) Patent No.: US 9,801,601 B2
(45) Date of Patent: Oct. 31, 2017

(54) METHOD AND SYSTEM FOR PERFORMING MULTI-BONE SEGMENTATION IN IMAGING DATA

(71) Applicant: LABORATOIRES BODYCAD INC., Québec (CA)

(72) Inventors: Geoffroy Rivet-Sabourin, Stoneham (CA); Vénérée Rakotomalala Randrianarisoa, Quebec (CA)

(73) Assignee: LABORATOIRES BODYCAD INC., Québec (CA)

( * ) Notice: Subject to any disclaimer, the term of this patent is extended or adjusted under 35 U.S.C. 154(b) by 142 days.

(21) Appl. No.: 14/982,029

(22) Filed: Dec. 29, 2015

(65) Prior Publication Data
US 2016/0275674 A1    Sep. 22, 2016

(51) Int. Cl.
*G06K 9/00* (2006.01)
*A61B 6/00* (2006.01)
*G06T 7/11* (2017.01)
*G06T 7/12* (2017.01)
(Continued)

(52) U.S. Cl.
CPC .............. *A61B 6/505* (2013.01); *G06T 7/11* (2017.01); *G06T 7/12* (2017.01); *G06T 7/136* (2017.01);
(Continued)

(58) Field of Classification Search
USPC ........ 382/100, 103, 106–107, 128–132, 154, 382/162, 168, 173, 181, 199, 232, 254,
(Continued)

(56) References Cited

U.S. PATENT DOCUMENTS

| | | | | | |
|---|---|---|---|---|---|
| 4,888,555 | A | * | 12/1989 | Vaughan | ............... G01R 33/58 324/300 |
| 5,005,578 | A | * | 4/1991 | Greer | ................... G01R 33/565 324/318 |

(Continued)

FOREIGN PATENT DOCUMENTS

| | | | | |
|---|---|---|---|---|
| CA | WO 2014165973 | * | 10/2014 | ............... G06T 7/60 |
| WO | 2013166592 A1 | | 11/2013 | |

(Continued)

OTHER PUBLICATIONS

Pohle et al., "Segmentation of medical images using adaptative region growing", SPIE Proceedings, vol. 4322, Medical Imaging 2001: Image processing, 1337, Jul. 3, 2001.

(Continued)

*Primary Examiner* — Seyed Azarian
(74) *Attorney, Agent, or Firm* — Marshall, Gerstein & Borun LLP

(57) ABSTRACT

A computer implemented method for performing bone segmentation in imaging data of a section of a body structure is provided. The method includes: Obtaining the imaging data including a plurality of 2D images of the section of the body structure; and performing a multiphase local-based hybrid level set segmentation on at least a subset of the plurality of 2D images by minimizing an energy functional including a local-based edge term and a local-based region term computed locally inside a local neighborhood centered at each pixel of each one of the 2D images on which the multiphase local-based hybrid level set segmentation is performed, the local neighborhood being defined by a Gaussian kernel whose size is determined by a scale parameter ($\sigma$).

23 Claims, 13 Drawing Sheets

(51) Int. Cl.
| | |
|---|---|
| G06T 7/174 | (2017.01) |
| G06T 7/136 | (2017.01) |
| A61B 5/00 | (2006.01) |
| A61B 5/055 | (2006.01) |
| A61B 6/03 | (2006.01) |

(52) U.S. Cl.
CPC .............. *G06T 7/174* (2017.01); *A61B 5/055* (2013.01); *A61B 5/4504* (2013.01); *A61B 5/4528* (2013.01); *A61B 6/032* (2013.01); *A61B 6/5211* (2013.01); *G06T 2207/10072* (2013.01); *G06T 2207/20036* (2013.01); *G06T 2207/20161* (2013.01); *G06T 2207/30008* (2013.01)

(58) Field of Classification Search
USPC ....... 382/266, 274, 276, 285–291, 305, 312; 324/309, 300; 378/4, 16, 21
See application file for complete search history.

(56) References Cited

U.S. PATENT DOCUMENTS

| | | | | |
|---|---|---|---|---|
| 5,545,995 | A * | 8/1996 | Schneider | G01R 33/56563 324/300 |
| 5,790,692 | A | 8/1998 | Price et al. | |
| 5,797,396 | A * | 8/1998 | Geiser | G06T 7/66 382/128 |
| 6,078,680 | A | 6/2000 | Yoshida et al. | |
| 6,078,688 | A | 6/2000 | Cox et al. | |
| 6,697,661 | B2 * | 2/2004 | Raghavan | G01R 33/285 324/309 |
| 6,965,235 | B1 | 11/2005 | Guclu et al. | |
| 7,282,723 | B2 | 10/2007 | Schomacker et al. | |
| 7,440,609 | B2 | 10/2008 | Von Berg et al. | |
| 7,587,073 | B2 | 9/2009 | Park | |
| 7,889,941 | B2 | 2/2011 | Piovano et al. | |
| 7,925,087 | B2 | 4/2011 | Slabaugh et al. | |
| 8,160,345 | B2 | 4/2012 | Pavlovskaia et al. | |
| 8,175,349 | B2 | 5/2012 | Jerebko et al. | |
| 8,189,889 | B2 | 5/2012 | Pearlstein et al. | |
| 8,253,802 | B1 | 8/2012 | Anderson et al. | |
| 8,275,443 | B2 | 9/2012 | Goldenberg et al. | |
| 8,306,305 | B2 | 11/2012 | Porat et al. | |
| 8,340,387 | B2 | 12/2012 | Zhang et al. | |
| 9,218,524 | B2 | 12/2015 | Wang et al. | |
| 2006/0222226 | A1 | 10/2006 | Xia et al. | |
| 2007/0086640 | A1 | 4/2007 | Luo et al. | |
| 2007/0088211 | A1 | 4/2007 | Cheng et al. | |
| 2008/0049999 | A1 | 2/2008 | Jerebko et al. | |
| 2008/0317308 | A1 | 12/2008 | Wu et al. | |
| 2009/0185746 | A1 | 7/2009 | Mian et al. | |
| 2010/0008576 | A1 | 1/2010 | Piramuthu | |
| 2010/0198063 | A1 | 8/2010 | Huber et al. | |
| 2011/0075927 | A1 | 3/2011 | Xu et al. | |
| 2011/0081056 | A1 | 4/2011 | Salafia | |
| 2011/0110567 | A1 | 5/2011 | Jiang | |
| 2011/0123090 | A1 | 5/2011 | Zerfass et al. | |
| 2011/0262054 | A1 | 10/2011 | Benson et al. | |
| 2012/0189185 | A1 | 7/2012 | Chen et al. | |
| 2013/0272594 | A1 | 10/2013 | Zelzer et al. | |
| 2014/0086465 | A1 | 3/2014 | Wu et al. | |

FOREIGN PATENT DOCUMENTS

| | | |
|---|---|---|
| WO | 2013166606 A1 | 11/2013 |
| WO | 2014165972 A1 | 10/2014 |
| WO | 2014165973 A1 | 10/2014 |

OTHER PUBLICATIONS

Mao et al., "Color image segmentation method based on region growing and ant colony clustering", WRI Global Congress on Intelligent Systems, p. 173-177, May 19, 2009.

Tilton, J.C., "Image segmentation by region growing and spectral clustering with a neural convergence criterion", Proceedings of the 1998 Geoscience and remote sensing symposium (ICGARSS. '98) Jul. 6, 1998.

Barberi et al., "A Transmit-Only/Receive-Only (TORO) RF System for High-Filed MRI/MRS Applications", Magnetic Resonance in Medicine 43:284-289, 2000.

Yang, "An image analysis system for measuring shape and motion of white blood cells from a sequence of fluorescent microscopy images", University of Oslo, Master Thesis, 1994, 128p.

Chunming Li et al., "A level set method for image segmentation in the presence of intensity inhomogeneities with application to MRI", IEEE Transactions on Image Processing, vol. 20, No. 7, pp. 2007-2012 Jul. 2011.

Nikos Paragios, Rachid Deriche, "Geodesic Active Regions: A new framework to deal with frame partition problems in computer vision", Computer Vision and Robotics Group (Robot Vis) of I.N.R.I.A., Doctoral Research, p. 1-20, 1996-1999.

Marcel Krcah et al. "Fully automatic and fast segmentation of the femur bone from 3D-CT images with no shape prior", ISBI 2011, p. 2087-2090.

D. Mumford & J. Shah, "Optimal Approximations by Piecewise Smooth Functions and Associated Variational Problems", Communications on Pure and Applied Mathematics, XLII(5): 577-685, 1989.

C. Li, C. Kao, J. Gore, and Z. Ding, Minimization of Region-Scalable Fitting Energy for Image Segmentation, IEEE Trans Image Process. Oct. 2008; 17(10): 1940-1949, 2008.

C. Li, C. Xu, C. Gui, and M. D. Fox. "Distance Regularized Level Set Evolution and its Application to Image Segmentation", IEEE Trans. Image Processing, vol. 19 (12), pp. 3243-3254, 2010.

C. Li, C. Xu, C. Gui, and M. D. Fox, "Level Set Evolution Without Re-initialization: A New Variational Formulation", CVPR 2005, 430-436 vol. 1, 2005.

L. J. Latecki, R. Lakämper, "Convexity Rule for Shape Decomposition Based on Discrete Contour Evolution", Computer Vision and Image Understanding (CVIU), vol. 73, pp. 441-454, 1999.

N. Paragios ,R. Deriche, "Geodesic active regions and level set methods for motion estimation and tracking", Computer Vision and Image Understanding (CVIU), vol. 97, Issue 3, Mar. 2005, pp. 259-282, 2005.

T. Chan, L. Vese, "Active contours without edges." IEEE Transactions on Image Processing, 10(2), 266-277, 2001.

T.F. Chan, Y. B. Sandberg, "Active contours without edges for Vector—valued Image.", Journal of Visual Communication and Image Representation 11, 130-141 2000.

T. F. Chan, L. A. Vese, "A Multiphase level set framework for image segmentation using the Mumford and Shah model." International Journal of Computer Vision 50(3), 271-293, 2002.

V. Randrianarisoa, J.-F. Bernier, R. Bergevin, "Detection of Multi-Part Objects by Top-Down Perceptual Grouping.", CRV 2005, Victoria, B.C., Canada, 536-543, 2005.

Weickert J., Scharr H., "A scheme for coherence-enhancing diffusion filtering with optimized rotation invariance," J. Vis. Commun. Image Represent., vol. 13, No. 1/2, pp. 103-118, 2002.

Paragios N, Deriche R., "Coupled Geodesic Active Regions for Image Segmentation: A Level Set Approach", Proceeding, ECCV '00 Proceedings of the 6th European Conference on Computer Vision—Part II, pp. 224-240, 2000.

D.J. Kroon, C.H. Slump, T.J. Maal, "Optimized anisotropic rotational invariant diffusion scheme on cone-beam CT", Med Image Comput Comput Assist Interv., 13(Pt 3):221-8, 2010.

P. Perona and J. Malik, "Scale-Space and Edge Detection Using Anisotropic Diffusion," IEEE Transactions on Pattern Analysis and Machine Intelligence, 12(7):629-639, Jul. 1990.

V. Caselles, F. Catté, T. Coll, F. Dibos, "A geometric model for active contours in image processing," Numerische Mathematik, vol. 66, Issue 1, pp. 1-31, Dec. 1993.

J Sauvola, M Pietikäinen : Adaptive document image binarization, Pattern recognition, vol. 33, pp. 225-236, 2000, Elsevier.

Timo Kohlberger et al., "Automatic Multi-organ Segmentation using Learning-Based Segmentation and Level set Optimization",

(56) References Cited

OTHER PUBLICATIONS

Medical Image Computing and Computer-Assisted Intervention, Miccai 2011, Springer Berllin Heidelberg, pp. 338-345.
Mesejo Pablo et al., << Biomedical image segmentation using geometric deformable models and metaheuristics >>, Computerized Medical Imaging and Graphics, vol. 43, Jul. 2015 (Jul. 2015), pp. 167-178, XP029244398, ISSN: 0895-6111, DOI: 10.1016/J.COMPMEDIMAG.2013.12.005.

* cited by examiner

METHOD AND SYSTEM FOR PERFORMING MULTI-BONE SEGMENTATION IN IMAGING DATA

TECHNICAL FIELD OF THE INVENTION

The present invention relates to the field of bone structure imaging for skeletal modelling. More particularly, it relates to a method for performing multi-bone segmentation in closely matching joints of a patient, as part of a bone imaging process.

BACKGROUND

There are several advantages that may occur from patient-specific orthopedic implants and surgeries including exact sizing of the implant according to the anatomy, such as reducing operating time, improving performance, etc.

When designing and conceiving patient-specific orthopedic implants and planning surgeries, including alignment guides, all relevant components of an anatomical structure, e.g. an articulation, are to be modeled and segmented with high precision. Precise modelling and segmentation in turn ensures that the resulting prostheses and alignment guides accurately fit the unique shape and size of the anatomical structure. Furthermore, segmentation of bones from 3D images is important to many clinical applications such as visualization, enhancement, disease diagnosis, implant design, cutting guide design, and surgical planning.

In the field of bone imaging, many imaging techniques and methods are known in the art in order to produce a skeletal model, such as a 3D skeletal model, of at least a portion of a body structure of a patient, such as a bone or series of bones on/between which an orthopedic implant is to be implanted.

For example and without being limitative, common imaging techniques, including magnetic resonance imaging (MRI), computed axial tomography (CAT scan), ultrasound, or the like are combined with three-dimensional image reconstruction tools, such as CAD software or the like, for the three-dimensional image reconstruction. In the case of bones with well-defined joints, known imaging techniques and three-dimensional image reconstruction tools are usually able to produce satisfactory models.

However, in the case of small and/or multiple adjacent bones such as, for example, bones of the hands and foot, where the distance between the bones is relatively small, thereby forming closely matching joints therebetween, and larger bones with outer edges closely matching one another, thereby also defining closely matching joints, such as hip bones or the like, known imaging techniques and three-dimensional image reconstruction tools often prove inadequate to perform the required individual multi-bone segmentation, i.e. the partitioning of a digital image into multiple segments in order to provide data that can be used for generating the three-dimensional image which clearly define the shape of each bone of the joints and is therefore more meaningful or easier to analyze. In fact, the failure of those well-known imaging techniques to segment these images is due to the challenging nature of the acquired images. For example, in CT imagery, when the boundaries of two bones are too close to each other, as described earlier, they tend to be diffused, which lower the contrast of the boundaries of the neighboring bones with respect to the background. Moreover, the bone structures have inhomogeneous intensities which involve an overlap between the distributions of the intensities within the regions.

In view of the above, there is a need for an improved method and system for performing bone segmentation which would be able to overcome or at least minimize some of the above-discussed prior art concerns.

BRIEF SUMMARY OF THE INVENTION

According to a general aspect, there is provided a computer implemented method for performing bone segmentation in imaging data of a section of a body structure. The method comprises:

Obtaining the imaging data including a plurality of 2D images of the section of the body structure; and Performing a multiphase local-based hybrid level set segmentation on at least a subset of the plurality of 2D images by minimizing an energy functional including a local-based edge term and a local-based region term computed locally inside a local neighborhood centered at each pixel of each one of the 2D images on which the multiphase local-based hybrid level set segmentation is performed, the local neighborhood being defined by a Gaussian kernel whose size is determined by a scale parameter ($\sigma$).

The minimization of the energy functional generates segmented blobs delimitating the regions of the 2D images, each one of the blobs substantially contouring one or more bones contained in the respective one of the 2D images. For instance, the segmented blobs are used to discriminate the background of the 2D images from the region(s) corresponding to the bones. The segmented blobs in each of the 2D images can be stacked to generate a plurality of 3D subvolumes, each one of the 3D subvolumes resulting from the combination of a plurality of corresponding segmented blobs. Each one of the 3D subvolumes corresponds to one or more bones. The plurality of 3D subvolumes can be combined to generate a 3D volume including a plurality of bones of the section of the body structure. The 3D volume is thus a 3D model of the bones of the section of the body structure.

In an embodiment, the local neighborhood is circular and performing the multiphase local-based hybrid level set segmentation further comprises: for each pixel of the 2D images, dynamically changing region descriptors based on a position of a center of the local neighborhood.

In an embodiment, the computer implemented method further comprises: selecting a value of $\lambda$ to adjust a performance of the multiphase local-based hybrid level set segmentation with $\lambda$ being greater than 0 and smaller than 1, wherein $\lambda$ multiplies the local-based edge term and $(1-\lambda)$ multiplies local-based region term.

In an embodiment, the computer implemented method further comprises: initializing the multiphase local-based hybrid level set segmentation with a contour obtained from a 3D adaptive thresholding, the contour being close to boundaries of the bones to be segmented.

In an embodiment, the 2D images include two phases and the energy functional is:

$$\mathcal{F}_{2\text{-}phase}(\phi,c,b) = (1-\lambda)\mathcal{E}_{region}(\phi,c,b) + \lambda\mathcal{E}_{edge}(\phi) + \mu \mathcal{R}_p(\phi)$$

where $\lambda$ is greater than or equal to 0 and smaller than or equal to 1, $\mu$ is a positive constant, b is a bias field accounting for intensity inhomogeneity, and c is a vector representing intensity-based constant values in disjoint regions, $$E_{edge}(\phi) = \nu \mathcal{L}_g(\phi) + \alpha \mathcal{A}_g(\phi) \quad (4)$$

wherein $\nu$ and $\alpha$ are normalization constants, $$\mathcal{L}_g(\phi) \triangleq \int g_{\sigma,\tau} \delta_\varepsilon(\phi) |\nabla \phi| dx,$$

$$\mathcal{A}_g(\phi) \triangleq \int g_{\sigma,\tau} \mathcal{H}_\varepsilon(-\phi) dx,$$

$$g_{\sigma,\tau} \triangleq \frac{1}{1 + f_{\sigma,\tau}},$$

$$f_{\sigma,\tau}(x) = \int K_\sigma(y-x) u_\tau(y) dy,$$

$$u_\tau \triangleq |\nabla G_\tau * I|^2$$

with $G_\tau$ being a Gaussian kernel with a standard definition $\tau$ and I being the image, $K_\sigma$, a kernel function computed by means of a truncated Gaussian function of the scale parameter ($\sigma$), $\rho$ being the radius of the local circular neighborhood:

$$K_\sigma(u) = \begin{cases} \frac{1}{a} e^{-|u|^2/2\sigma^2}, & |u| \leq \rho \\ 0, & \text{otherwise} \end{cases} \text{ and}$$

$$H_\varepsilon(\phi) = \frac{1}{2}\left[1 + \frac{2}{\pi}\arctan\left(\frac{\phi}{\varepsilon}\right)\right]$$

with $\varepsilon$ being a parameter; and $$E_{region}(\phi,c,b) = \int (\Sigma_{i=1}^N (\int K_\sigma(y-x)|I(x)-b(y)c_i|^2 dy) \mathcal{M}_i(\phi(x))) dx$$

$\mathcal{M}_i$ is a membership function of each region $\Omega_i$, and is defined as:

$$\mathcal{M}_2(\phi) = \mathcal{H}_\varepsilon(\phi)$$

$$\mathcal{M}_2(\phi) = 1 - \mathcal{H}_\varepsilon(\phi)$$

wherein $\mathcal{R}_p$ is a regularisation term:

$$\mathcal{R}_p(\phi) = \int p(|\nabla\phi|) dx$$

and the minimization of the hybrid energy functional $\mathcal{F}$ is carried out by gradient descent method:

$$\frac{\partial \phi}{\partial t} = -\frac{\partial F_{2\_phase}}{\partial \phi}$$

In another embodiment, the energy functional is:

$$\mathcal{F}_{multiphase}(\Phi,c,b) = (1-\lambda) E_{region}(\Phi,c,b) + \lambda E_{edge}(\Phi) + \mu \mathcal{R}_p(\Phi)$$

where $\lambda$ is greater than or equal to 0 and smaller than or equal to 1, $\mu$ is a positive constant, b is a bias field accounting for intensity inhomogeneity, c is a vector representing intensity-based constant values in disjoint regions, and $\phi$ is a vector formed by k level set functions $\phi i$, $i=1 \ldots k$ for k regions or phases;

$$\Phi = (\phi_1(y), \ldots, \phi_k(y))$$

and a number of the level set functions to be used is at least equal to:

$$k = \log_2(\mathcal{N})$$

where $\log_2$ is the logarithm to the base 2 and N is the number of the regions to be segmented in the image.

$$E_{region}(\Phi,c,b) = \int (\Sigma_{i=1}^N e_i(x) M_i(\Phi)x)) dx$$

With:

$$e_i(x) = \int K_\sigma |I(x) - b(y)c_i|^2 dy, \, i=1, \ldots, k$$

with $K_\sigma$, a kernel function computed by means of a truncated Gaussian function of standard deviation $\sigma$, referred to as the scale parameter, $\mathcal{M}_i$ is a membership function of each region $\Omega_i$, and is defined as:

$$M_i(\Phi) = M_i(\phi_1(y), \ldots, \phi_k(y)) = \begin{cases} 1, & y \in \Omega_i \\ 0, & \text{else} \end{cases}$$

$$E_{edge}(\Phi) = \nu \mathcal{L}_g(\Phi) + \alpha \mathcal{A}_g(\Phi)$$

Where:

$$\mathcal{L}_g(\Phi) = \Sigma_{j=1}^k \mathcal{L}_g(\phi_j)$$

$$\mathcal{A}_g(\Phi) = \Sigma_{j=1}^k \mathcal{A}_g(\phi_j)$$

wherein $\nu$ and $\alpha$ are normalization constants,
wherein $\mathcal{R}_p$ is a regularisation term:

$$\mathcal{R}_p(\phi) = \int p(|\nabla\phi|) dx$$

and the minimization of the multiphase hybrid energy functional $\mathcal{F}_{multiphase}$ by gradient descent method:

$$\frac{\partial \phi_1}{\partial t} = -\frac{\partial Fmult_{iphase}(\Phi)}{\partial \phi_1}, \ldots, \frac{\partial \phi_k}{\partial t} = -\frac{\partial Fmu_{ltiphase}(\Phi)}{\partial \phi_k}.$$

In an embodiment, the computer implemented method further comprises: identifying regions of interest (ROIs) on at least the subset of the plurality of 2D images of the section of the body structure; and performing the multiphase local-based hybrid level set segmentation on the regions of interest (ROIs).

According to another general aspect, there is provided a computer implemented method for performing bone segmentation in imaging data of at least a section of a body structure including a plurality of bones using anatomical knowledge data relative to the section of the body structure of the imaging data, the method comprising:

Obtaining the imaging data including a plurality of 2D images of the section of the body structure;

Generating primary image data from the imaging data using an image preprocessing including identifying regions of interest (ROIs) in the 2D images;

Generating secondary segmented image data including a plurality of 2D binary images with segmented blobs by performing a multiphase local-based hybrid level set segmentation on the regions of interest (ROIs) by minimizing an energy functional including a local-based edge term and a local-based region term computed locally inside a local neighborhood centered at each point of a respective one of the regions of interest (ROIs), the local neighborhood being defined by a Gaussian kernel;

Generating a 3D volume including a plurality of 3D subvolumes from the segmented blobs of the secondary segmented image data; and Associating an anatomical component to each one of the 3D subvolumes using the anatomical knowledge data relative to the section of the body structure of the imaging data.

In an embodiment, the image preprocessing further comprises performing a 3D adaptive thresholding processing to define thresholded blobs in the 2D images and generating binary masks from the thresholded blobs obtained by the 3D adaptive thresholding processing. The plurality of 2D images are greyscale images and the 3D adaptive thresholding processing can include the steps of:

For at least a sample of the plurality of 2D greyscale images:
Dividing each one of the 2D greyscale images of at least the sample in a plurality of sections;
Computing a local pixel intensity section threshold for each one of the sections;
Computing a global image pixel intensity threshold for each one of the 2D greyscale images of at least the sample using the local pixel intensity section thresholds computed for each one of the sections;
Computing a global volume pixel intensity threshold using the global image pixel intensity thresholds; and
Applying the global volume pixel intensity threshold to each one of the 2D greyscale images of the plurality of 2D greyscale images.

The global image pixel intensity threshold for each one of the 2D greyscale images of at least the sample can be computed as a maximum of the local pixel intensity thresholds for the corresponding image. The global volume pixel intensity threshold from the global image pixel intensity thresholds can be computed as a mean of the global image pixel intensity thresholds minus 1.5 times a standard deviation of the global image pixel intensity thresholds [mean (global image pixel intensity thresholds)−1.5std(global image pixel intensity thresholds)]. The image preprocessing can comprise computing thresholded blobs in the images following the 3D adaptive thresholding processing and creating binary masks from the thresholded blobs. Identifying regions of interest (ROIs) in the 2D images can comprise selecting regions in the 2D greyscale images of the imaging data including at least one of a respective one of the thresholded blobs and a respective one of the binary masks generated from the thresholded blobs.

In an embodiment, generating secondary segmented image data can comprise performing a blob masking validation following the multiphase local-based hybrid level set segmentation, the multiphase local-based hybrid level set segmentation generating a plurality of unmasked blobs, and wherein the blob masking validation comprises:

Applying the binary masks to the unmasked blobs to obtain masked blobs;
Determining at least one perceptual grouping property of each one of the masked blobs and the unmasked blobs;
For each corresponding pair of masked blobs and unmasked blobs,
Comparing the at least one perceptual grouping property of the masked blob to the at least one perceptual grouping property of the corresponding one of unmasked blobs; and
Selecting the one of the masked blob and the corresponding one of unmasked blobs having the highest perceptual grouping property as the segmented blob of the secondary segmented image data.

The computer implemented method can further comprise initializing the multiphase local-based hybrid level set segmentation with the binary masks.

Performing the multiphase local-based hybrid level set segmentation on the regions of interest (ROIs) can comprise generating binary subimages including the segmented blobs and the method can further comprise merging the binary subimages to generate a respective one of the 2D binary images including the segmented blobs.

In an embodiment, generating secondary segmented image data comprises stacking the 2D binary images.

In an embodiment, the image preprocessing further comprises:
Determining an initial image including at least one region of interest and determining a final image including at least one region of interest; and
Selecting a subset of 2D images including the initial image, the final image, and the images extending therebetween, wherein the primary image data consists of the subset of 2D images including the regions of interest (ROIs).

The computer implemented method of any one of claims 6 to 13, wherein identifying anatomical components in the 3D volume comprises:
Computing at least one subvolume feature for each one of the 3D subvolumes;
For each one of the 3D subvolumes, carrying out a bone identification processing comprising:
Identifying a closest one of the bones and comparing the at least one subvolume feature to features of the anatomical knowledge data corresponding to the closest one of the bones;
If the at least one subvolume feature for the respective one of the 3D subvolumes substantially corresponds to the features of the anatomical knowledge data for the closest one of the bones, associating the respective one of the 3D subvolumes to the closest one of the bones;
Otherwise, applying a selective 3D bone separation to the respective one of the 3D subvolumes and generating new 3D subvolumes.

Identifying anatomical components in the 3D volume can further comprise:
Identifying a 3D anatomical point of interest within the 3D volume;
Identifying a 3D subvolume closest to the 3D anatomical point of interest; and
Performing sequentially the bone identification processing by proximity to a last one of associated 3D subvolumes, starting from the 3D subvolume closest to the 3D anatomical point of interest.

The computer implemented method of one of claims 14 and 15, wherein the 3D volume generated from the 2D binary images of the secondary segmented image data is a first 3D volume and the method further comprises:
Carrying out a 2D blob separation on the secondary segmented image data and generating a second 3D volume by stacking binary images obtained following the 2D blob separation; and
wherein identifying anatomical components is performed on the second 3D volume.

Carrying out a 2D blob separation can comprise:
For each one of the segmented blobs of the secondary segmented image data:
Creating straight segments from the contours of the respective one of the segmented blobs;
Identifying points of interest using the straight segments;
If there is at least one point of interest, identifying at least one bone attachment location close to the at least one point of interest; and separating the respective one of the segmented blobs by local morphological erosion along the at least one bone attachment location.

Identifying points of interest using the straight segments can comprise:

Determining a length of the straight segments and an angle between consecutive ones of the straight segments, the consecutive one of the straight segments sharing a common point;

For each pair of consecutive straight segments ($s_1$, $s_2$), computing a relevance measure ($K_{relevance}$):

$$K_{relevance} = \frac{\beta(s_1, s_2) l(s_1) l(s_2)}{l(s_1) + l(s_2)}$$

wherein $\beta(s_1, s_2)$ is the angle between the two consecutive straight segments $s_1$ and $s_2$;

$l(s_1)$ and $l(s_2)$ are lengths of the two consecutive straight segments $s_1$ and $s_2$ respectively;

Comparing the computed relevance measure to a predetermined threshold; and

If the computed relevance measure meets the predetermined relevance threshold, identifying the common point as being a point of interest.

Identifying at least one bone attachment location close to the at least one point of interest can comprise:

Identifying if a respective one of the points of interest belongs to a linear bone attachment location defined by a pair of points of interest; and, for each identified linear bone attachment location, separating the respective one of the segmented blobs comprises performing a linear local morphological erosion along a line extending between the points of interest defining the linear bone attachment location;

otherwise, identifying the respective one of the points of interest as a punctual bone attachment location and separating the respective one of the segmented blobs comprises performing local morphological erosion around the punctual bone attachment location.

Identifying a pair of points of interest can comprise: for each potential pair of points of interest, grouping the points of interest in a pair and computing a distance separating two grouped points of the pair, comparing the computed distance to a predetermined distance threshold; and if the computed distance meets the predetermined distance threshold, associating the potential pair of interest points as being one linear bone attachment location.

In an embodiment, the local neighborhood is circular and performing the multiphase local-based hybrid level set segmentation further comprises: for each pixel of the regions of interest (ROIs), dynamically changing region descriptors based on a position of a center of the local neighborhood.

In an embodiment, the computer implemented method further comprises: selecting a value of $\lambda$ to adjust the performance of the multiphase local-based hybrid level set segmentation with $\lambda$ being greater than 0 and smaller than 1, wherein $\lambda$ multiplies the local-based edge term and $(1-\lambda)$ multiplies local-based region term.

In an embodiment, the regions of interest (ROIs) include two phases and the energy functional is:

$$\mathcal{F}_{2\text{-}phase}(\phi,c,b) = (1-\lambda)\mathcal{E}_{region}(\phi,c,b) + \lambda \mathcal{E}_{edge}(\phi) + \mu \mathcal{R}_p(\phi)$$

where $\lambda$ is greater than or equal to 0 and smaller than or equal to 1, $\mu$ is a positive constant, b is a bias field accounting for intensity inhomogeneity, and c is a vector representing intensity-based constant values in disjoint regions, $$\mathcal{E}_{edge}(\phi) = \nu \mathcal{L}_g(\phi) + \alpha \mathcal{A}_g(\phi) \quad (4)$$

wherein $\nu$ and $\alpha$ are normalization constants, $$\mathcal{L}_g(\phi) \triangleq \int g_{\sigma,\tau} \delta_\varepsilon(\phi) |\nabla \phi| dx,$$

$$\mathcal{A}_g(\phi) \triangleq \int g_{\sigma,\tau} \mathcal{H}_\varepsilon(-\delta) dx,$$

$$g_{\sigma,\tau} \triangleq \frac{1}{1+f_{\sigma,\tau}},$$

$$f_{\sigma,\tau}(x) = \int K_\sigma(y-x) u_\tau(y) dy,$$

$$u_\tau \triangleq |\nabla G_\tau * I|^2$$

with $G_\tau$ being a Gaussian kernel with a standard definition $\tau$ and I being the image, $K_\sigma$, a kernel function computed by means of a truncated Gaussian function of the scale parameter ($\sigma$), $\rho$ being the radius of the local circular neighborhood:

$$K_\sigma(u) = \begin{cases} \frac{1}{a} e^{-|u|^2/2\sigma^2}, & |u| \leq \rho \\ 0, & \text{otherwise} \end{cases}$$

and $$H_\varepsilon(\phi) = \frac{1}{2}\left[1 + \frac{2}{\pi}\arctan\left(\frac{\phi}{\varepsilon}\right)\right]$$

with $\varepsilon$ being a parameter; and $$\mathcal{E}_{region}(\phi,c,b) = \int (\Sigma_{i=1}^N (\int K_\sigma(y-x)|I(x)-b(y)c_i|^2 dy) \mathcal{M}_i(\phi(x)) dx$$

$\mathcal{M}_i$ is a membership function of each region $\delta_i$, and is defined as:

$$\mathcal{M}_1(\phi) = \mathcal{H}_\varepsilon(\phi)$$

$$\mathcal{M}_2(\phi) = 1 - \mathcal{H}_\varepsilon(\phi)$$

wherein $\mathcal{R}_p$ is a regularisation term:

$$\mathcal{R}_p(\phi) = \int p(|\nabla \phi|) dx$$

and the minimization of the hybrid energy functional $\mathcal{F}$ is carried out by gradient descent method:

$$\frac{\partial \phi}{\partial t} = -\frac{\partial F_{2\_phase}}{\partial \phi}.$$

In another embodiment, the energy functional is:

$$\mathcal{F}_{multiphase}(\Phi,c,b) = (1-\lambda)\mathcal{E}_{region}(\Phi,c,b) + \lambda \mathcal{E}_{edge}(\Phi) + \mu \mathcal{R}_p(\Phi)$$

where $\lambda$ is greater than or equal to 0 and smaller than or equal to 1, $\mu$ is a positive constant, b is a bias field accounting for intensity inhomogeneity, c is a vector representing intensity-based constant values in disjoint regions, and $\phi$ is a vector formed by k level set functions $\phi i$, $i=1 \ldots k$ for k regions or phases;

$$\Phi = (\phi_1(y), \ldots, \phi_k(y))$$

and a number of the level set functions to be used is at least equal to:

$$k=\log_2(\mathcal{N})$$

where $\log_2$ is the logarithm to the base 2 and N is the number of the regions to be segmented in the image.

$$\mathcal{E}_{region}(\Phi,c,b)=\int \Sigma_{i=1}^N e_i(x) M_i(\Phi)x))dx$$

With:

$$e_i(x)=\int K_\sigma |I(x)-b(y)c_i|^2 dy, \; i=1,\ldots,k$$

with $K_\sigma$, a kernel function computed by means of a truncated Gaussian function of standard deviation $\sigma$, referred to as the scale parameter, $\mathcal{M}_i$ is a membership function of each region $\Omega_i$, and is defined as:

$$M_i(\Phi) = M_i(\phi_1(y), \ldots, \phi_k(y)) = \begin{cases} 1, & y \in \Omega_i \\ 0, & \text{else} \end{cases}$$

$$E_{edge}(\Phi) = \nu \mathcal{L}_g(\Phi) + \alpha \mathcal{A}_g(\Phi)$$

Where:

$$\mathcal{L}_g(\Phi)=\Sigma_{j=1}^k(\mathcal{L}_g(\phi_j))$$

$$\mathcal{A}_g(\Phi)=\Sigma_{j=1}^k \mathcal{A}_g(\phi_j)$$

wherein $\nu$ and $\alpha$ are normalization constants,
wherein $\mathcal{R}_p$ is a regularisation term:

$$\mathcal{R}_p(\Phi)=\int p(|\nabla\Phi|)dx$$

and the minimization of the multiphase hybrid energy functional $\mathcal{F}_{multiphase}$ by gradient descent method:

$$\frac{\partial \phi_1}{\partial t} = -\frac{\partial Fmult_{iphase}(\Phi)}{\partial \phi_1}, \ldots, \frac{\partial \phi_k}{\partial t} = -\frac{\partial Fmu_{ltiphase}(\Phi)}{\partial \phi_k}.$$

According to a general aspect, there is provided a computer implemented method for performing bone segmentation in imaging data of at least a section of a body structure including a plurality of bones using anatomical knowledge data relative to the section of the body structure of the imaging data. The method comprises:
  Obtaining the imaging data including a plurality of 2D greyscale images of the section of the body structure;
  Generating primary image data from the imaging data using an image preprocessing including:
  Performing a 3D adaptive thresholding processing to define thresholded blobs in each of the 2D greyscale images;
  Generating binary masks from the thresholded blobs; and
  Identifying regions of interest (ROIs) in the 2D greyscale images of the imaging data using the binary masks generated from the thresholded blobs;
  Generating secondary segmented image data including a plurality of 2D binary images with segmented blobs by:
  Carrying out a segmentation on the regions of interest (ROIs) to obtain a plurality of unmasked blobs;
  Applying the binary masks to the unmasked blobs to obtain masked blobs;
  Determining at least one perceptual grouping property of each one of the masked blobs and the unmasked blobs;
  For each corresponding pair of masked blobs and unmasked blobs,
  Comparing the at least one perceptual grouping property of the masked blob to the at least one perceptual grouping property of the corresponding one of the unmasked blobs; and
  Selecting the one of the masked blob and the corresponding one of unmasked blobs having the highest perceptual grouping property as the segmented blob of the secondary segmented image data;
  Generating a 3D volume including a plurality of 3D subvolumes from the segmented blobs of the secondary segmented image data; and
  Associating an anatomical component to each one of the 3D subvolumes using the anatomical knowledge data relative to the section of the body structure of the imaging data.

In an embodiment, the 3D adaptive thresholding processing includes the steps of:
  For at least a sample of the plurality of 2D greyscale images:
  Dividing each one of the 2D greyscale images of at least the sample in a plurality of sections;
  Computing a local pixel intensity section threshold for each one of the sections;
  Computing a global image pixel intensity threshold for each one of the 2D greyscale images of at least the sample using the local pixel intensity section thresholds computed for each one of the sections;
  Computing a global volume pixel intensity threshold using the global image pixel intensity thresholds; and
  Applying the global volume pixel intensity threshold to each one of the 2D greyscale images of the plurality of 2D greyscale images.

The global image pixel intensity threshold for each one of the 2D greyscale images of at least the sample can be computed as a maximum of the local pixel intensity thresholds for the corresponding image.

The global volume pixel intensity threshold from the global image pixel intensity thresholds can be computed as a mean of the global image pixel intensity thresholds minus 1.5 times a standard deviation of the global image pixel intensity thresholds [mean(global image pixel intensity thresholds)−1.5std(global image pixel intensity thresholds)].

Identifying regions of interest (ROIs) in the 2D greyscale images can comprise selecting regions in the 2D greyscale images of the imaging data including at least one of a respective one of the thresholded blobs and a respective one of the binary masks generated from the thresholded blobs.

The segmentation can be a multiphase local-based hybrid level set segmentation performed by minimizing an energy functional including a local-based edge term and a local-based region term computed locally inside a local neighborhood centered at each point of a respective one of the regions of interest (ROIs), the local neighborhood being defined by a Gaussian kernel and the method further comprises initializing the multiphase local-based hybrid level set segmentation with the binary masks.

In an embodiment, performing the segmentation on the regions of interest (ROIs) comprises generating binary subimages including the segmented blobs and the method further comprises merging the binary subimages to generate a respective one of the 2D binary images including the segmented blobs.

In an embodiment, generating secondary segmented image data comprises stacking the 2D binary images.

In an embodiment, the image preprocessing further comprises:

Determining an initial image including at least one region of interest and determining a final image including at least one region of interest; and Selecting a subset of 2D images including the initial image, the final image, and the images extending therebetween, wherein the primary image data consists of the subset of 2D images including the regions of interest (ROIs).

In an embodiment, identifying anatomical components in the 3D volume comprises:

Computing at least one subvolume feature for each one of the 3D subvolumes;

For each one of the 3D subvolumes, carrying out a bone identification processing comprising:

Identifying a closest one of the bones and comparing the at least one subvolume feature to features of the anatomical knowledge data corresponding to the closest one of the bones;

If the at least one subvolume feature for the respective one of the 3D subvolumes substantially corresponds to the features of the anatomical knowledge data for the closest one of the bones, associating the respective one of the 3D subvolumes to the closest one of the bones;

Otherwise, applying a selective 3D bone separation to the respective one of the 3D subvolumes and generating new 3D subvolumes.

Identifying anatomical components in the 3D volume can further comprise:

Identifying a 3D anatomical point of interest within the 3D volume;

Identifying a 3D subvolume closest to the 3D anatomical point of interest; and

Performing sequentially the bone identification processing by proximity to a last one of associated 3D subvolumes, starting from the 3D subvolume closest to the 3D anatomical point of interest.

The 3D volume generated from the 2D binary images of the secondary segmented image data can be a first 3D volume and the method can further comprise:

Carrying out a 2D blob separation on the secondary segmented image data and generating a second 3D volume by stacking binary images obtained following the 2D blob separation; and wherein identifying anatomical components is performed on the second 3D volume.

Carrying out a 2D blob separation can comprise:

For each one of the segmented blobs of the secondary segmented image data:

Creating straight segments from the contours of a respective one of the segmented blobs;

Identifying points of interest using the straight segments;

If there is at least one point of interest, identifying at least one bone attachment location close to the at least one point of interest; and separating the respective one of the segmented blobs by local morphological erosion along the at least one bone attachment location.

Identifying points of interest using the straight segments can comprise:

Determining a length of the straight segments and an angle between consecutive ones of the straight segments, the consecutive one of the straight segments sharing a common point;

For each pair of consecutive straight segments ($s_1$, $s_2$), computing a relevance measure ($K_{relevance}$):

$$K_{relevance} = \frac{\beta(s_1, s_2) l(s_1) l(s_2)}{l(s_1) + l(s_2)}$$

wherein $\beta(s_1, s_2)$ is the angle between the two consecutive straight segments $s_1$ and $s_2$;

$l(s_1)$ and $l(s_2)$ are lengths of the two consecutive straight segments $s_1$ and $s_2$ respectively;

Comparing the computed relevance measure to a predetermined threshold; and

If the computed relevance measure meets the predetermined relevance threshold, identifying the common point as being a point of interest.

Identifying at least one bone attachment location close to the at least one point of interest can comprise:

Identifying if a respective one of the points of interest belongs to a linear bone attachment location defined by a pair of points of interest; and, for each identified linear bone attachment location, separating the respective one of the segmented blobs comprises performing a linear local morphological erosion along a line extending between the points of interest defining the linear bone attachment location;

otherwise, identifying the respective one of the points of interest as a punctual bone attachment location and separating the respective one of the segmented blobs comprises performing local morphological erosion around the punctual bone attachment location.

Identifying a pair of points of interest can comprise: for each potential pair of points of interest, grouping the points of interest in a pair and computing a distance separating two grouped points of the pair, comparing the computed distance to a predetermined distance threshold; and if the computed distance meets the predetermined distance threshold, associating the potential pair of interest points as being one linear bone attachment location.

In an embodiment, the local neighborhood is circular and performing the multiphase local-based hybrid level set segmentation further comprises: for each pixel of the regions of interest (ROIs), dynamically changing region descriptors based on a position of a center of the local neighborhood.

In an embodiment, the computer implemented method further comprises: selecting a value of $\lambda$ to adjust a performance of the multiphase local-based hybrid level set segmentation with $\lambda$ being greater than 0 and smaller than 1, wherein $\lambda$ multiplies the local-based edge term and $(1-\lambda)$ multiplies local-based region term.

In an embodiment, the regions of interest (ROIs) include two phases and the energy functional is:

$$\mathcal{F}_{2-phase}(\phi,c,b) = (1-\lambda)\mathcal{E}_{region}(\phi,c,b) + \lambda \mathcal{E}_{edge}(\phi) + \mu \mathcal{R}_p(\phi)$$

where $\lambda$ is greater than or equal to 0 and smaller than or equal to 1, $\mu$ is a positive constant, b is a bias field accounting for intensity inhomogeneity, and c is a vector representing intensity-based constant values in disjoint regions, $$\mathcal{E}_{edge}(\phi) = \nu \mathcal{L}_g(\phi) + \alpha \mathcal{A}_g(\phi) \qquad (4)$$

wherein $\nu$ and $\alpha$ are normalization constants, $$\mathcal{L}_g(\phi) \triangleq \int g_{\sigma,\tau} \delta(\phi) |\nabla \phi| dx,$$

$$\mathcal{A}_g(\phi) \triangleq \int g_{\sigma,\tau} \mathcal{H}(-\phi) dx,$$

-continued $$g_{\sigma,\tau} \triangleq \frac{1}{1+f_{\sigma,\tau}},$$

$$f_{\sigma,\tau}(x) = \int K_\sigma(y-x)u_\tau(y)dy,$$

$$u_\tau \triangleq |\nabla G_\tau * I|^2$$

with $G_\tau$ being a Gaussian kernel with a standard definition $\tau$ and I being the image, $K_\sigma$, a kernel function computed by means of a truncated Gaussian function of the scale parameter ($\sigma$), $\rho$ being the radius of the local circular neighborhood:

$$K_\sigma(u) = \begin{cases} \frac{1}{a}e^{-|u|^2/2\sigma^2}, & |u| \leq \rho \\ 0, & \text{otherwise} \end{cases}$$

and $$H_\varepsilon(\phi) = \frac{1}{2}\left[1 + \frac{2}{\pi}\arctan\left(\frac{\phi}{\varepsilon}\right)\right]$$

with $\ominus$ being a parameter; and $$\mathcal{E}_{region}(\phi,c,b) = \int (\Sigma_{i=1}^N \int K_\sigma(y-x)|I(x)-b(y)c_i|^2 dy) \mathcal{M}_i(\phi(x))dx$$

$\mathcal{M}_i$ is a membership function of each region $\Omega_i$, and is defined as:

$$\mathcal{M}_1(\phi) = \mathcal{H}_\varepsilon(\phi)$$

$$\mathcal{M}_2(\phi) = 1 - \mathcal{H}_\varepsilon(\phi)$$

wherein $\mathcal{R}_p$ is a regularisation term:

$$\mathcal{R}_p(\phi) = \int p(|\nabla \phi|)dx$$

and the minimization of the hybrid energy functional $\mathcal{F}$ is carried out by gradient descent method:

$$\frac{\partial \phi}{\partial t} = -\frac{\partial F_{2\,phase}}{\partial \phi}.$$

In another embodiment, the energy functional is:

$$\mathcal{F}_{multiphase}(\Phi,c,b) = (1-\lambda)\mathcal{E}_{region}(\Phi,c,b) + \lambda \mathcal{E}_{edge}(\Phi) + \mu \mathcal{R}_p(\Phi)$$

where $\lambda$ is greater than or equal to 0 and smaller than or equal to 1, $\mu$ is a positive constant, b is a bias field accounting for intensity inhomogeneity, c is a vector representing intensity-based constant values in disjoint regions, and $\phi$ is a vector formed by k level set functions $\phi_i$, $i=1 \ldots k$ for k regions or phases;

$$\Phi = (\phi_1(y), \ldots, \phi_k(y))$$

and a number of the level set functions to be used is at least equal to:

$$k = \log_2(\mathcal{N})$$

where $\log_2$ is the logarithm to the base 2 and N is the number of the regions to be segmented in the image.

$$\mathcal{E}_{region}(\Phi,c,b) = \int \Sigma_{i=1}^N e_i(x) M_i(\Phi)(x)) dx$$

With:

$$e_i(x) = \int K_\sigma |I(x) - b(y)c_i|^2 dy, \; i=1, \ldots, k$$

with $K_\sigma$, a kernel function computed by means of a truncated Gaussian function of standard deviation $\sigma$, referred to as the scale parameter, $\mathcal{M}_i$ is a membership function of each region $\Omega_i$, and is defined as:

$$M_i(\Phi) = M_i(\phi_1(y), \ldots, \phi_k(y)) = \begin{cases} 1, & y \in \Omega_i \\ 0, & \text{else} \end{cases}$$

$$\mathcal{E}_{edge}(\Phi) = \nu \mathcal{L}_g(\Phi) + \alpha \mathcal{A}_g(\Phi)$$

Where:

$$\mathcal{L}_g(\Phi) = \Sigma_{j=1}^k \mathcal{L}_g(\phi_j)$$

$$\mathcal{A}_g(\Phi) = \Sigma_{j=1}^k \mathcal{A}_g(\phi_j)$$

wherein $\nu$ and $\sigma$ are normalization constants,
wherein $\mathcal{R}_p$ is a regularisation term:

$$\mathcal{R}_p(\Phi) = \int p(|\nabla \phi|)dx$$

and the minimization of the multiphase hybrid energy functional $\mathcal{F}_{multiphase}$ by gradient descent method:

$$\frac{\partial \phi_1}{\partial t} = -\frac{\partial F mult_{iphase}(\Phi)}{\partial \phi_1}, \ldots, \frac{\partial \phi_k}{\partial t} = -\frac{\partial F mu_{ltiphase}(\Phi)}{\partial \phi_k}.$$

According to still another general aspect, there is provided a system for generating segmentation data segmentation from imaging data of at least a section of a body structure including a plurality of bones using anatomical knowledge data relative to the section of the body structure of the imaging data. The system comprises:

a processing unit having a processor and a memory;

an image preprocessing module stored on the memory and executable by the processor, the image preprocessing module having program code that when executed, generates primary image data from the imaging data using an image preprocessing process, the primary image data including regions of interest in images of the imaging data;

a multi-bone segmentation module stored on the memory and executable by the processor, the multi-bone segmentation module having a program code that when executed, generates a 3D volume by performing a multiphase local-based hybrid level set segmentation to obtain a plurality of segmented blobs and combining the segmented blobs to obtain the 3D volume including a plurality of 3D subvolumes, the multiphase local-based hybrid level set segmentation being carried out on each one of on the regions of interest (ROIs) by minimizing an energy functional including a local-based edge term and a local-based region term computed locally inside a local neighborhood centered at each point of a respective one of the regions of interest (ROIs), the local neighborhood being defined by a Gaussian kernel and generating a 3D volume following the multiphase local-based hybrid level set segmentation; and an anatomical component identification module stored on the memory and executable by the processor, the anatomical component identification module having a program code that, when executed, generates tertiary segmented imaging data through identification of the subvolumes defined in the 3D volume and identification of bones defined by the subvolumes.

In an embodiment, the program code of the anatomical component identification module, when executed, performs further 3D bone separation of at least one of the subvolumes.

According to a further general aspect, there is provided a computer implemented method for 3D adaptive thresholding of a 3D grayscale volume image including a plurality of 2D greyscale images. The method comprises:

Selecting a subset of "N" 2D greyscale images from the plurality of 2D greyscale images, wherein "N" is smaller or equal to a number of images of the plurality of 2D greyscale images;

Dividing each one of the "N" 2D greyscale images in "M" sections;

Computing a set of "M" local pixel intensity thresholds for each one of the "N" 2D greyscale images divided into "M" sections;

Computing a global image pixel intensity threshold for each one of the "N" 2D greyscale images to obtain "N" global image pixel intensity thresholds;

Computing a global volume pixel intensity threshold from the "N" global image pixel intensity thresholds; and Applying the global volume pixel intensity threshold to threshold each one of the plurality of 2D greyscale images of the 3D grayscale volume image.

In an embodiment, the global image pixel intensity threshold for each one of the "N" 2D greyscale images is computed as a maximum of the "M" local pixel intensity thresholds for the corresponding one of the "N" 2D greyscale images.

In an embodiment, the global volume pixel intensity threshold from the "N" global image pixel intensity thresholds is computed as a mean of the "N" global image pixel intensity thresholds minus 1.5 times a standard deviation of the "N" global image pixel intensity thresholds [mean("N" global image pixel intensity thresholds)−1.5std("N" global image pixel intensity thresholds)].

According to another general aspect, there is provided a computer implemented method for performing bone segmentation in imaging data of at least a section of a body structure including a plurality of bones using anatomical knowledge data relative to the section of the body structure of the imaging data. The method comprises:

Obtaining the imaging data including a plurality of 2D images of the section of the body structure;

Generating primary image data from the imaging data using an image preprocessing including identifying regions of interest (ROIs) in the 2D images;

Generating secondary segmented image data including a plurality of 2D binary images with segmented blobs by performing a segmentation on the regions of interest (ROIs);

Carrying out a 2D blob separation on the secondary segmented image data comprising:

For each one of the segmented blobs of the secondary segmented image data:

Creating straight segments from the contours of the respective one of the segmented blobs;

Identifying points of interest using the straight segments;

If there is at least one point of interest, identifying at least one bone attachment location close to the at least one point of interest; and separating the respective one of the segmented blobs by local morphological erosion along the at least one bone attachment location; and Stacking binary images obtained following the 2D blob separation to generate a 3D volume including a plurality of 3D subvolumes; and Associating an anatomical component to each one of the 3D subvolumes using the anatomical knowledge data relative to the section of the body structure of the imaging data.

In an embodiment, identifying points of interest using the straight segments comprises:

Determining a length of the straight segments and an angle between consecutive ones of the straight segments, the consecutive one of the straight segments sharing a common point;

For each pair of consecutive straight segments $(s_1, s_2)$, computing a relevance measure $(K_{relevance})$:

$$K_{relevance} = \frac{\beta(s_1, s_2) l(s_1) l(s_2)}{l(s_1) + l(s_2)}$$

wherein $\beta(s_1, s_2)$ is the angle between the two consecutive straight segments $s_1$ and $s_2$;

$l(s_1)$ and $l(s_2)$ are lengths of the two consecutive straight segments $s_1$ and $s_2$ respectively;

Comparing the computed relevance measure to a predetermined threshold; and

If the computed relevance measure meets the predetermined relevance threshold, identifying the common point as being a point of interest.

Identifying at least one bone attachment location close to the at least one point of interest can comprise:

Identifying if a respective one of the points of interest belongs to a linear bone attachment location defined by a pair of points of interest; and, for each identified linear bone attachment location, separating the respective one of the segmented blobs comprises performing a linear local morphological erosion along a line extending between the points of interest defining the linear bone attachment location;

otherwise, identifying the respective one of the points of interest as a punctual bone attachment location and separating the respective one of the segmented blobs comprises performing local morphological erosion around the punctual bone attachment location.

Identifying a pair of points of interest can comprise: for each potential pair of points of interest, grouping the points of interest in a pair and computing a distance separating two grouped points of the pair, comparing the computed distance to a predetermined distance threshold; and if the computed distance meets the predetermined distance threshold, associating the potential pair of interest points as being one linear bone attachment location.

In an embodiment, the image preprocessing further comprises performing a 3D adaptive thresholding processing to define thresholded blobs in the 2D images and generating binary masks from the thresholded blobs obtained by the 3D adaptive thresholding processing. The plurality of 2D images can be greyscale images and wherein the 3D adaptive thresholding processing can include the steps of:

For at least a sample of the plurality of 2D greyscale images:

Dividing each one of the 2D greyscale images of at least the sample in a plurality of sections;

Computing a local pixel intensity section threshold for each one of the sections;

Computing a global image pixel intensity threshold for each one of the 2D greyscale images of at least the sample using the local pixel intensity section thresholds computed for each one of the sections;

Computing a global volume pixel intensity threshold using the global image pixel intensity thresholds; and Applying the global volume pixel intensity threshold to each one of the 2D greyscale images of the plurality of 2D greyscale images.

The global image pixel intensity threshold for each one of the 2D greyscale images of at least the sample can be computed as a maximum of the local pixel intensity thresholds for the corresponding image.

The global volume pixel intensity threshold from the global image pixel intensity thresholds can be computed as a mean of the global image pixel intensity thresholds minus 1.5 times a standard deviation of the global image pixel intensity thresholds [mean(global image pixel intensity thresholds)−1.5std(global image pixel intensity thresholds)].

In an embodiment, the image preprocessing can comprise computing thresholded blobs in the images following the 3D adaptive thresholding processing and creating binary masks from the thresholded blobs.

Identifying regions of interest (ROIs) in the 2D images can comprise selecting regions in the 2D greyscale images of the imaging data including at least one of a respective one of the thresholded blobs and a respective one of the binary masks generated from the thresholded blobs.

Generating secondary segmented image data can comprise performing a blob masking validation following the segmentation, the segmentation generating a plurality of unmasked blobs, and wherein the blob masking validation comprises:

Applying the binary masks to the unmasked blobs to obtain masked blobs;

Determining at least one perceptual grouping property of each one of the masked blobs and the unmasked blobs;

For each corresponding pair of masked blobs and unmasked blobs,

Comparing the at least one perceptual grouping property of the masked blob to the at least one perceptual grouping property of the corresponding one of the unmasked blobs; and Selecting the one of the masked blob and the corresponding one of the unmasked blobs having the highest perceptual grouping property as the segmented blob of the secondary segmented image data.

Segmentation can comprise a multiphase local-based hybrid level set segmentation carried out by minimizing an energy functional including a local-based edge term and a local-based region term computed locally inside a local neighborhood centered at each pixel of each one of the 2D images on which the multiphase local-based hybrid level set segmentation is performed, the local neighborhood being defined by a Gaussian kernel whose size is determined by a scale parameter; and the method further comprises initializing the multiphase local-based hybrid level set segmentation with the binary masks.

Performing the multiphase local-based hybrid level set segmentation on the regions of interest (ROIs) can comprise generating binary subimages including the segmented blobs and the method further comprises merging the binary subimages to generate a respective one of the 2D binary images including the segmented blobs.

In an embodiment, the image preprocessing further comprises:

Determining an initial image including at least one region of interest and determining a final image including at least one region of interest; and Selecting a subset of 2D images including the initial image, the final image, and the images extending therebetween, wherein the primary image data consists of the subset of 2D images including the regions of interest (ROIs).

In an embodiment, identifying anatomical components in the 3D volume comprises:

Computing at least one subvolume feature for each one of the 3D subvolumes;

For each one of the 3D subvolumes, carrying out a bone identification processing comprising:

Identifying a closest one of the bones and comparing the at least one subvolume feature to features of the anatomical knowledge data corresponding to the closest one of the bones;

If the at least one subvolume feature for the respective one of the 3D subvolumes substantially corresponds to the features of the anatomical knowledge data for the closest one of the bones, associating the respective one of the 3D subvolumes to the closest one of the bones;

Otherwise, applying a selective 3D bone separation to the respective one of the 3D subvolumes and generating new 3D subvolumes.

Identifying anatomical components in the 3D volume can further comprise:

Identifying a 3D anatomical point of interest within the 3D volume;

Identifying a 3D subvolume closest to the 3D anatomical point of interest; and

Performing sequentially the bone identification processing by proximity to a last one of associated 3D subvolumes, starting from the 3D subvolume closest to the 3D anatomical point of interest.

In an embodiment, the local neighborhood is circular and performing the multiphase local-based hybrid level set segmentation further comprises: for each pixel of the regions of interest (ROIs), dynamically changing region descriptors based on a position of a center of the local neighborhood.

The computer implemented method further comprises: selecting a value of $\lambda$ to adjust a performance of the multiphase local-based hybrid level set segmentation with $\lambda$ being greater than 0 and smaller than 1, wherein $\lambda$ multiplies the local-based edge term and $(1-\lambda)$ multiplies local-based region term.

In an embodiment, the regions of interest (ROIs) include two phases and the energy functional is:

$$\mathcal{F}_{2\text{-}phase}(\phi,c,b)=(1-\lambda)\mathcal{E}_{region}(\phi,c,b)+\lambda\mathcal{E}_{edge}(\phi)+\mu\mathcal{R}_p(\phi)$$

where $\lambda$ is greater than or equal to 0 and smaller than or equal to 1, $\mu$ is a positive constant, b is a bias field accounting for intensity inhomogeneity, and c is a vector representing intensity-based constant values in disjoint regions, $$\mathcal{E}_{edge}(\phi)=\nu\mathcal{L}_g(\phi)+\alpha\mathcal{A}_g(\phi) \quad (4)$$

wherein $\nu$ and $\alpha$ are normalization constants, $$\mathcal{L}_g(\phi) \triangleq \int g_{\sigma,\tau}\, \delta(\phi)|\nabla\phi|dx,$$

$$\mathcal{A}_g(\phi) \triangleq \int g_{\sigma,\tau}\, \mathcal{H}(-\phi)dx,$$

$$g_{\sigma,\tau} \triangleq \frac{1}{1+f_{\sigma,\tau}},$$

-continued $$f_{\sigma,\tau}(x) = \int K_\sigma(y-x)u_\tau(y)dy,$$

$$u_\tau \overset{\Delta}{=} |\nabla G_\tau * I|^2$$

with $G_\tau$ being a Gaussian kernel with a standard definition $\tau$ and I being a gradient of the image,
$K_\sigma$, a kernel function computed by means of a truncated Gaussian function of standard deviation $\sigma$, $\rho$ being the radius of the local circular neighborhood:

$$K_\sigma(u) = \begin{cases} \frac{1}{a}e^{-|u|^2/2\sigma^2}, & |u| \le \rho \\ 0, & \text{otherwise} \end{cases}$$

and $$H_\varepsilon(\phi) = \frac{1}{2}\left[1 + \frac{2}{\pi}\arctan\left(\frac{\phi}{\varepsilon}\right)\right]$$

with $\varepsilon$ being a parameter; and $$\mathcal{E}_{region}(\phi,c,b) = \int (\Sigma_{i=1}^{N}(\int K_\sigma(y-x)|I(x)-b(y)c_i|^2 dy (\mathcal{M}_i(\phi(x))dx$$

$\mathcal{M}_i$ is a membership function of each region $\Omega_i$, and is defined as:

$$\mathcal{M}_1(\phi) = \mathcal{H}_\varepsilon(\phi)$$

$$\mathcal{M}_2(\phi) = 1 - \mathcal{H}_\varepsilon(\phi)$$

wherein $\mathcal{R}_p$ is a regularisation term:

$$\mathcal{R}_p(\phi) = \int p(|\nabla \phi|)dx$$

and the minimization of the hybrid energy functional $\mathcal{F}$ is carried out by gradient descent method:

$$\frac{\partial \phi}{\partial t} = -\frac{\partial F_{2\,phase}}{\partial \phi}.$$

In another embodiment, the energy functional is:

$$\mathcal{F}_{multiphase}(\Phi,c,b) = (1-\lambda)\mathcal{E}_{region}(\Phi,c,b) + \lambda \mathcal{E}_{edge}(\Phi) + \mu \mathcal{R}_p(\Phi)$$

where $\lambda$ is greater than or equal to 0 and smaller than or equal to 1, $\mu$ is a positive constant, b is a bias field accounting for intensity inhomogeneity, c is a vector representing intensity-based constant values in disjoint regions, and $\phi$ is a vector formed by k level set functions $\phi_i$, $i=1 \ldots k$ for k regions or phases;

$$\Phi = (\phi_1(y), \ldots, \phi_k(y))$$

and a number of the level set functions to be used is at least equal to:

$$k = \log_2(\mathcal{N})$$

where $\log_2$ is the logarithm to the base 2 and N is the number of the regions to be segmented in the image.

$$\mathcal{E}_{region}(\Phi,c,b) = \int \Sigma_{i=1}^{N} e_i(x)M_i(\Phi)x))dx$$

With:

$$e_j(x) = \int K_\sigma |I(x)-b(y)c_i|^2 dy, \, i=1, \ldots, k$$

with $K_\sigma$, a kernel function computed by means of a truncated Gaussian function of standard deviation $\sigma$, referred to as the scale parameter, $\mathcal{M}_i$ is a membership function of each region $\Omega_i$, and is defined as:

$$M_i(\Phi) = M_i(\phi_1(y), \ldots, \phi_k(y)) = \begin{cases} 1, & y \in \Omega_i \\ 0, & \text{else} \end{cases}$$

$$\mathcal{E}_{edge}(\Phi) = \nu \mathcal{L}_g(\Phi) + \alpha \mathcal{A}_g(\Phi)$$

Where:

$$\mathcal{L}_g(\Phi) = \Sigma_{j=1}^{k} \mathcal{L}_g(\phi_j)$$

$$\mathcal{A}_g(\Phi) = \Sigma_{j=1}^{k} \mathcal{A}_g(\phi_j)$$

wherein $\nu$ and $\alpha$ are normalization constants,
wherein $\mathcal{R}_p$ is a regularisation term:

$$\mathcal{R}_p(\phi) = \int p(|\nabla \phi|)dx$$

and the minimization of the multiphase hybrid energy functional $\mathcal{F}_{multiphase}$ by gradient descent method:

$$\frac{\partial \phi_1}{\partial t} = -\frac{\partial Fmult_{iphase}(\Phi)}{\partial \phi_1}, \ldots, \frac{\partial \phi_k}{\partial t} = -\frac{\partial Fmu_{ltiphase}(\Phi)}{\partial \phi_k}.$$

The present document refers to a number of documents, the contents of which are hereby incorporated by reference in their entirety.

In this specification, the terms "grayscale image" and "grayscale subimage" are intended to mean acquired images prior to the level set segmentation, either prior to or following a filtering process. The term "grayscale subimage" is intended to mean a region of interest (ROI) of a "grayscale image". The term "binary image" is intended to mean the images following segmentation, i.e. including one or several blobs. The term "binary subimage" is intended to mean a section of a binary image including or centered on at least one blob. In this specification, the term "blob" is intended to mean a single disconnected object in a binary image. In this specification, the term "anatomical bone boundaries" is intended to mean the contours of the physical bones of a section of a body structure.

BRIEF DESCRIPTION OF THE DRAWINGS

Other objects, advantages and features will become more apparent upon reading the following non-restrictive description of embodiments thereof, given for the purpose of exemplification only, with reference to the accompanying drawings in which:

FIG. 5A shows the grayscale image to be segmented, FIG. 5B shows the image following the bone segmentation without applying binary masks, and FIG. 5C shows the image following the bone segmentation with application of binary masks.

FIGS. 7A, 7B, 7C, 7D, and 7E are greyscale ROIs of bones of an ankle prior to and following multi-bone segmentation, wherein FIG. 7A shows an initialization of a multiphase local-based hybrid level set segmentation with an arbitrary rectangular contour, FIG. 7B shows an initialization of the multiphase local-based hybrid level set segmentation with a mask, FIG. 7C shows the results of the bone segmentation with the multiphase local-based hybrid level set segmentation initialized with the arbitrary rectangular contour of FIG. 7A, FIG. 7D shows the results of the bone segmentation with the multiphase local-based hybrid level set segmentation initialized with the mask of FIG. 7B wherein the multiphase local-based hybrid level set segmentation is carried out with the same number of iterations than FIG. 7C, FIG. 7E shows the results of the bone segmentation with the multiphase local-based hybrid level set segmentation initialized with the arbitrary rectangular contour of FIG. 7A but carried out with a higher number of iterations than for FIGS. 7C and 7D.

FIGS. 8A, 8B, and 8C are binary images resulting from the bone segmentation with the multiphase local-based hybrid level set segmentation, wherein FIG. 8A is a binary image showing unmasked (original) blobs resulting from the multiphase local-based hybrid level set segmentation, FIG. 8B is the binary image of FIG. 8A with a binary mask applied thereon to obtained masked blobs, i.e. following blob masking, and FIG. 8C is the binary image of FIG. 8A being selected as segmented blob with a substantially noise free background.

DETAILED DESCRIPTION

In the following description, the same numerical references refer to similar elements. The embodiments mentioned in the present description are embodiments only, given solely for exemplification purposes.

Moreover, although the embodiments of the method and system for performing multi-bone segmentation consist of certain configurations as explained and illustrated herein, not all of these configurations are essential and thus should not be taken in their restrictive sense. It is to be understood, as also apparent to a person skilled in the art, that other suitable components and cooperation thereinbetween, as well as other suitable configurations, may be used for the method and system for performing multi-bone segmentation, as will be briefly explained herein and as can be easily inferred herefrom by a person skilled in the art.

As mentioned above, segmentation of bones from 3D images is important to many clinical applications such as visualization, enhancement, disease diagnosis, patient-specific implant design, cutting guide design, and surgical planning. The bones of a body structure, e.g. an articulation, are to be segmented with high precision.

Figure 1:
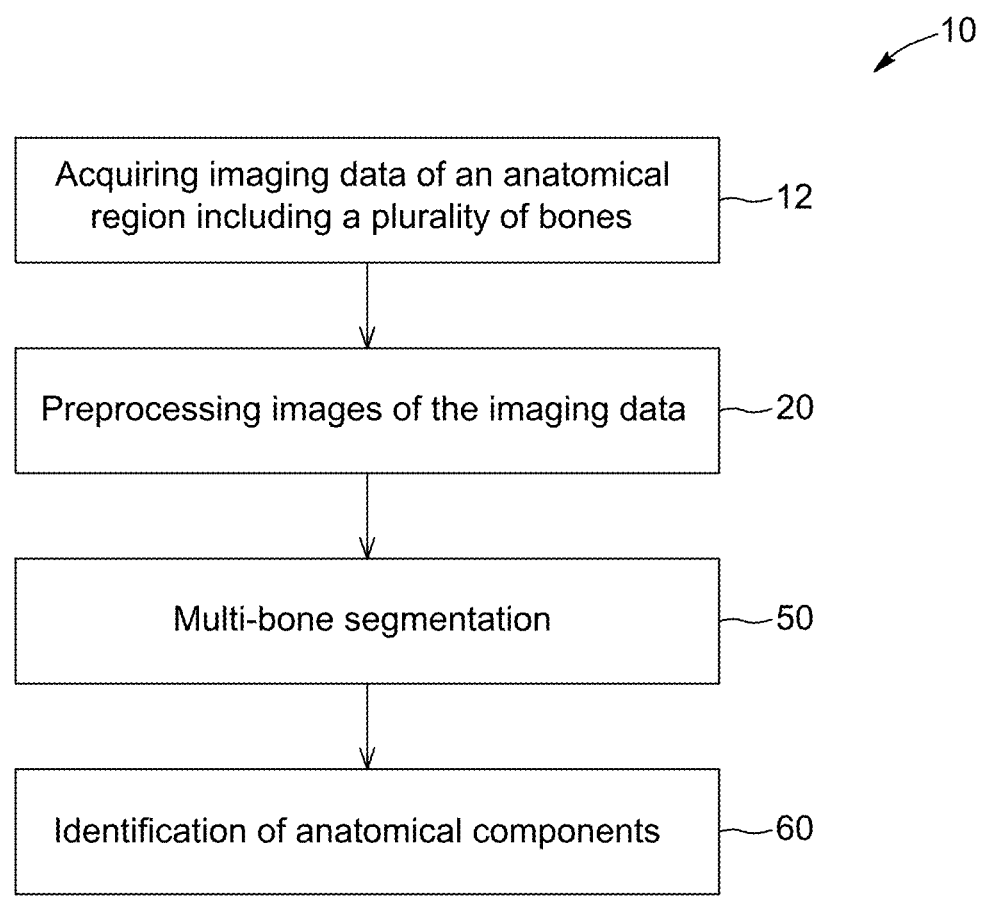
FIG. 1 is a flowchart of sequential general steps of a method for performing multi-bone segmentation in imaging data according to an embodiment.

Referring generally to FIG. 1, in accordance with one embodiment, there is provided a method 10 for performing multi-bone segmentation in imaging data of an anatomical region under study. The object of the method 10 is to generate data which can be used for creating a three-dimensional (3D) model in which each bone of the anatomical region is clearly distinguishable from the contiguous bones. At a high level, the method 10 includes the sequential steps of acquiring imaging data 12 to create a 3D grayscale volume image of an anatomical region under study including a plurality of bones (i.e. a body structure), performing an image preprocessing 20 on the acquired imaging data to generate primary image data, performing a subsequent multi-bone segmentation 50, including a multiphase local-based hybrid level set segmentation, on the primary image data to obtain at least one set of secondary segmented image data (in some implementations, two sets of secondary segmented image data are obtained) and, finally, performing an anatomical component identification processing 60 using anatomical knowledge data relative to the section of the body structure in order to generate tertiary segmented image data. The tertiary segmented image data can be used to generate a 3D bone reconstruction of the section of the body structure, i.e. the three-dimensional (3D) model in which each bone of the anatomical region is clearly distinguishable from the contiguous bones.

Each one of the above enumerated steps of the method 10 for performing multi-bone segmentation in body structure imaging data will now be described in more details below. The imaging data includes a plurality of 2D greyscale images of the body structure.

One skilled in the art will easily understand that the step of acquiring/obtaining imaging data 12 refers to the acquisition of bone structure data of at least the section of the body structure of the patient to be studied. It can be performed using an imaging apparatus operating according to any known image acquisition process or method. In an embodiment, the imaging data are acquired using computed axial tomography (CAT scan or CT scan). One skilled in the art will however understand that, in an alternative embodiment, the imaging data can be obtained using other known imaging techniques, such as, without being limitative, magnetic resonance imaging (MRI), ultrasound, or the like.

The 3D grayscale volume image, created from the imaging data acquiring step 12, is a common form of medical imaging scans, especially CT and MRI. The 3D grayscale volume image, or the body structure imaging data, includes a series of two-dimensional (2D) slices of the scanned body structure (or a plurality of 2D images) along one plane or direction, such as the sagittal, coronal, or transverse plane, with respect to the body structure, which can be referred to as the segmentation axis. In an embodiment, the thickness of each slices can be between about 0.6 mm and 1 mm with no or negligible spacing between the slices. One skilled in the art will however understand that, in an alternative embodiment, the slices can however be thinner or thicker than the above mentioned range. The thickness and spacing of the slices can be selected based on the body structure under study including the size of the bones contained in the section of the body structure. In an embodiment, each one of the bone structure images corresponds to a respective slice and is a 2D image. Thus, the volume of the section of the body structure is represented as a set of 2D grayscale images, extending substantially parallel to one another.

One skilled in the art will also understand that, in an embodiment, the acquisition of the imaging data 12 can be done according to multiple planes or directions with the data being combined or merged, as described in patent publication WO2013/166592, published Nov. 14, 2013, which is incorporated by reference herein. For example, a first set of images may be acquired along a first plane, such as the sagittal plane, with missing information being provided using data acquired along a second plane, such as the coronal plane. It should be understood that any suitable plane can be used as the first plane or second plane, the above example being given solely for exemplary purposes. Moreover, other combinations or techniques to optimize the use of data along more than one orientation will be readily understood by those skilled in the art. In an embodiment where the acquisition of the imaging data 12 is performed according to multiple planes, in the steps described below, the imaging data are subsequently segmented according to the segmentation axis extending along the plane in which the series of slices to be analyzed extend.

Following the image acquisition step 12, the body structure image data including a plurality of 2D images, corresponding to slices extending along at least one segmentation axis, are processed to perform multi-bone segmentation through sequential execution of the image preprocessing 20, the multi-bone segmentation 50 including the multiphase local-based hybrid level set segmentation, and the anatomical component identification processing 60.

Figure 2A:
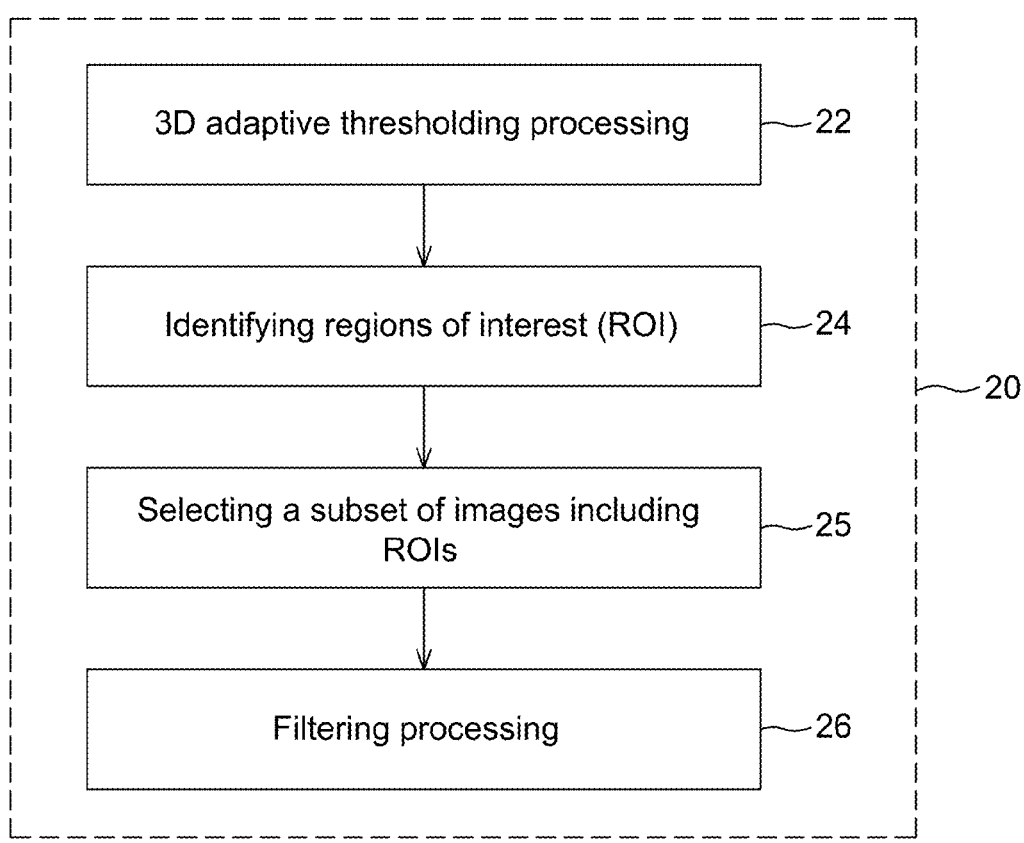
FIG. 2A is a flowchart of sequential steps of an image preprocessing of the method for performing multi-bone segmentation in imaging data according to FIG. 1, in accordance with an embodiment.
Figure 2B:
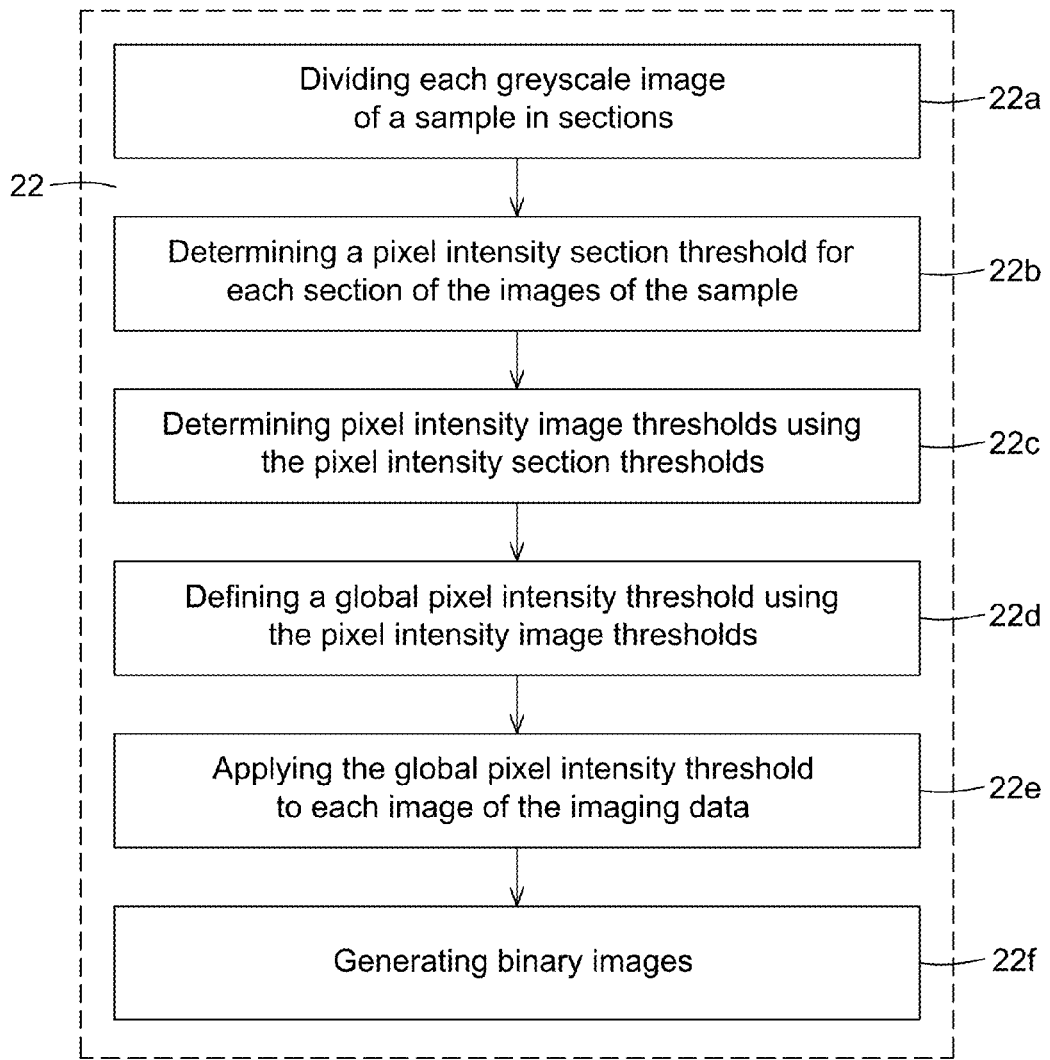
FIG. 2B is a flowchart of sequential steps of a 3D adaptive thresholding processing of the image preprocessing of FIG. 2A, in accordance with an embodiment.

Referring to FIGS. 2A and 2B, in the embodiment shown, the image preprocessing 20 includes a combination of 3D adaptive thresholding processing 22, region of interest (ROI) identification 24, selection of a subset of images including ROIs 25, and filtering processing 26, being performed sequentially to obtain primary image data from the unprocessed bone structure imaging data. In an embodiment, the primary image data includes a plurality of 2D images. However, if the image preprocessing 20 includes the selection of a subset of images based on the initial and final slices including ROIs, the number of 2D images in the primary image data is smaller than the number of 2D images in the original body structure image data.

Referring to FIG. 2B, in the embodiment shown, the 3D adaptive thresholding processing 22 is performed by determining a global volume pixel intensity threshold for converting the grayscale images of the unprocessed bone structure imaging data into binary images. In an embodiment, the global volume pixel intensity threshold can be determined using a sample of "N" of the grayscale images corresponding to slices of the imaging data. The use of a sample of the images for determining the global volume pixel intensity threshold for the 3D grayscale volume image allows the consumption of less processing power to perform the 3D adaptive thresholding processing 22, as opposed to the use of each one of the images of the imaging data. One skilled in the art will however understand that, in an alternative embodiment, the entire set of images can also be used in order to determine the global volume pixel intensity threshold. The 3D adaptive thresholding processing can include a step of selecting a sample of images from the bone structure imaging data. In a non-limitative embodiment, the sample is a uniformly distributed sample of the images corresponding to a slice of the imaging data. For example and without being limitative, the sample of images can be one image for each ten images of the imaging data. Once the global volume pixel intensity threshold is determined, the latter is subsequently applied to all of the 2D images of the imaging data which constitute the 3D grayscale volume image.

Still referring to FIG. 2B, in an embodiment, the pixel intensity threshold of each one of the images of the sample of images, referred to as the global image pixel intensity threshold, is determined by first dividing each grayscale image of the sample in a plurality of sections 22a, such as, without being limitative, rectangular sections of 50 pixels by 50 pixels, 100 pixels by 100 pixels, or the like, and then, determining a pixel intensity section threshold for each one of the sections 22b. The pixel intensity section threshold can be seen as a local threshold as its value may change from a section to another of the image. Therefore, a set of "M" local pixel intensity thresholds is obtained for a single image which corresponds to "M" pixel intensity section thresholds, "M" being the number of sections for each grayscale image. In an embodiment, the pixel intensity section threshold is determined using Otsu's method, which is well known to those skilled in the art and need not be described herein. One skilled in the art will understand that, in an alternative embodiment, other methods or techniques, different from the above mentioned Otsu's method, can be used for determining a pixel intensity threshold for each one of the sections. For instance and without being limitative, the following methods can be carried out: histogram shape, clustering, entropy object attribute, spatial, Pun thresholding, Kapur thresholding, fuzzy sets, etc.

In an embodiment, once the set of "M" local pixel intensity thresholds of the image are determined, a global image pixel intensity threshold is determined 22c for the image. In an embodiment, the global image pixel intensity threshold is determined by selecting the maximum of the set of "M" local pixel intensity thresholds of the corresponding image. It is appreciated that other methods or techniques, different from the above mentioned method, can be used for determining the global image pixel intensity threshold. Thus, for each image of the sample including "N" images, a global image pixel intensity threshold is then computed, which leads to generate a set of "N" global image pixel intensity thresholds for the "N" images of the sample.

Once the set of "N" global image pixel intensity thresholds is determined, a single global volume pixel intensity threshold for the 3D grayscale volume image is determined 22d using the formula below:

Global volume pixel intensity threshold=mean("N" global image pixel intensity thresholds)−(1.5× std("N" global image pixel intensity thresholds))

where mean("N" global image pixel intensity thresholds) corresponds to the mean of the set of "N" global image pixel intensity thresholds of the sample of images and std(set of "N" global image pixel intensity thresholds) corresponds to the standard deviation of the set of "N" global image pixel intensity thresholds of the sample of "N" images. One skilled in the art will understand that, in an alternative embodiment, a formula different from the one described above may be used in order to determine the global volume pixel intensity threshold from the set of "N" global image pixel intensity thresholds.

The above-described 3D adaptive thresholding combines local and global pixel intensity thresholds from a set of image samples of a 3D grayscale volume image in order to compute a single global volume pixel intensity threshold for the whole 3D grayscale volume image generated from all the 2D images of the imaging data. Moreover, the combination of local and global pixel intensity thresholds is suitable for 3D volume image thresholding with intensity inhomogeneity.

The global volume pixel intensity threshold is applied to the 3D grayscale volume image, i.e. to each one of the 2D images of the imaging data 22e, including the images of the sample of images, in order to complete the 3D adaptive thresholding processing 22. Following application of the global volume pixel intensity threshold, a 2D binary image is generated for each one of the images of the imaging data 22e, i.e. for each slice of the 3D grayscale volume image.

Even though in the embodiment described below, the 3D adaptive thresholding processing 22 is performed prior to a multiphase local-based hybrid segmentation, it is appreciated that it can be performed prior to any other suitable segmentation.

At least some of the binary images include blobs, which may include one or more bones. In the present specification, in order to distinguish the blobs obtained from 3D adaptive thresholding processing from blobs that will be obtained from the level set segmentation, the blobs obtained from 3D adaptive thresholding processing will be referred to as "thresholded blobs", i.e. blobs obtained after the 3D adaptive thresholding processing, while the blobs obtained from the level set segmentation will be referred to as "segmented blobs", i.e. blobs obtained after the segmentation and, more particularly, in an embodiment, the multiphase level set segmentation.

Thus, following the 3D adaptive thresholding processing, thresholded blobs in the binary images are identified. Morphological post-processing can be applied on these binary images in order to get closed thresholded blobs. The 3D adaptive thresholding processing can be seen as a coarse segmentation as each individual blob in each 2D binary image may contain pixels belonging to more than one bone. Each individual thresholded blob in each of 2D binary images is then identified and used as a binary mask. These binary masks have three main functions. First, they are used to extract/identify regions of interest (ROI) 24 from the grayscale images. Second, they are used to initialize the multiphase local-based hybrid level set function 50a, as will be described in more details below in reference to FIG. 6. Third, they are applied on the binary segmented images 50c in order to eliminate remaining background noise after the multiphase local-based hybrid segmentation 50b, as will be described in more details below also in reference to FIG. 6.

Referring back now to FIG. 2A, regions of interest (ROI) are then identified in each one of the grayscale images, i.e. region of interest identification 24 is carried out using the binary masks from the thresholded blobs of the binary images obtained by the 3D adaptive thresholding processing 22. The ROIs are potential grayscale regions containing one or more than one bone. Thus, each one of the ROIs includes at least one of a respective one of the thresholded blobs and a respective one of the binary masks generated from the thresholded blobs. As will be described in more details below, the multiphase local-based hybrid segmentation is applied to each of these ROIs in order to assign the segmented pixels to a single bone 60. Therefore, the subsequent multiphase local-based hybrid segmentation can be seen as a finer segmentation than the 3D adaptive thresholding processing 22.

The grayscale ROIs are subimages that will be segmented during the multi-bone segmentation 50 and the resulting blobs will be used as input to the anatomical component identification processing 60, which will be described in further details below. The blobs obtained from the multi-bone segmentation 50 are different from the blobs obtained following the 3D adaptive thresholding processing 22, which are referred to as "thresholded blobs".

Then, to reduce the following processing time, a subset of images is retrieved 25 by identifying a first one of the 2D grayscale images including at least one ROI and a last one of the 2D grayscale images including at least one ROI and selecting the images inbetween and including the first and the last images, i.e. the initial and the final images. The images before the initial image and the images after the final image are free of ROI, i.e. do not contain pixels belonging to a bone. For instance, the original set of images can include 512 images with image 183 being the first one to include a ROI and image 347 being the last one to include a ROI. Thus, the subset of images includes image 183 to 347. The following processing steps are performed on 165 images instead of 512 images. The determination of a subset of images including the initial and the final images and the images extending inbetween is an optional step.

Thus, the binary masks obtained from the 3D adaptive thresholding processing 22 are used to select unprocessed grayscale ROIs, in the set of greyscale images of the unprocessed bone structure imaging data including the initial and the final images and the images extending inbetween.

Figure 3A:
FIGS. 3A and 3B are greyscale regions of interest (ROIs) showing a plurality of bones of an ankle respectively prior to and following a filtering processing of the image preprocessing of FIG. 2A.
Figure 3B:
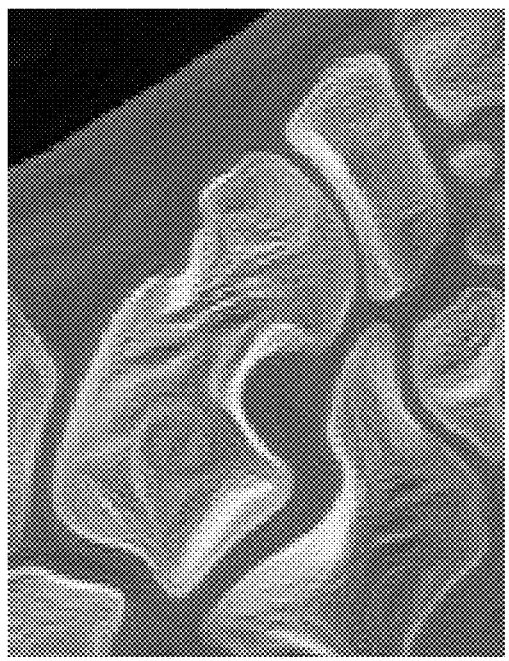

In an embodiment, the image preprocessing process 20 further includes a filtering processing 26, which is carried out on the subset of greyscale ROIs. In an embodiment, the filtering processing 26 is performed on each one of the greyscale ROIs of the subset of images, using an anisotropic coherence filtering process which is, once again, well known to those skilled in the art and need not be described herein. The anisotropic coherence filtering process reduces noise and increases the contrast at the boundary of the bones in each one of the grayscale ROIs, as shown in FIGS. 3A, 3B. FIG. 3A shows an original greyscale ROI while FIG. 3B shows the same ROI following the filtering process. The contrast around the boundary of the bones in FIG. 3B is enhanced with respect to the background in comparison with unprocessed FIG. 3A and the noise along the boundary of the bones is reduced.

In an embodiment, the filtering processing 26 is performed on the ROIs of the subset of the images. One skilled in the art will understand that, in an alternative embodiment, the filtering processing 26 can be performed on each entire image of the subset of images, rather than on the ROIs.

Moreover, it will be understood that, in an alternative embodiment, the filtering processing 26 can be performed using a filtering process or method different than the above mentioned anisotropic coherence filtering process, which also allows the above mentioned reduction of the noise and increase of the contrast at the boundaries of the bones in each one of the greyscale ROIs of the subset. Following the filtering processing 26, a plurality of filtered greyscale ROIs or images is obtained.

The image preprocessing process 20 generates primary image data, e.g. a subset of filtered greyscale 2D images with ROIs or greyscale 2D images with filtered ROIs, from an entire set of images including unprocessed greyscale imaging data. However, in order to produce highly relevant data as is required to obtain an accurate 3D bone model, the 2D images from the primary image data require additional bone segmentation, which is provided by the following steps of the method described below.

Referring back to FIG. 1, the multi-bone segmentation method 10 further comprises a multi-bone segmentation 50 wherein a multiphase local-based hybrid level set segmentation is carried out. The multiphase local-based hybrid level set segmentation is carried out on each ROI of the 2D images of the primary image data in order to generate secondary segmented image data including a plurality of 2D binary images. In an embodiment, the multiphase local-based hybrid level set segmentation generates a first set of secondary segmented image data.

There exists two major classes of level set methods for image segmentation: region-based models and edge-based models.

Region-based level sets rely on using region descriptor as intensity mean, Gaussian distribution or texture attribute of the regions and can be effective to detect objects in images whose gradient is not well defined, i.e. with weak and smooth boundary. Most of region-based level set methods rely on computing two global region descriptors for all pixels of the whole image, one for foreground pixels and one for background pixels. Therefore, they are effective when the image intensities are homogenous. However, when there are strong intensity inhomogeneities in the images, there can be an overlap between the distributions of the intensities in the regions. Therefore, it is impossible to compute global region descriptors to guide the evolution of the contour.

To overcome the non-homogeneity of the images, local region-based level sets have been proposed in the literature. In this approach, the region descriptor is computed locally inside a local circular neighborhood centered at each point of the whole image. This local circular neighborhood is designed by means of a Gaussian kernel, whose size is referred to as the scale parameter. Therefore, the region descriptors vary with the center of each local circular neighborhood and change dynamically over the image. A unique radius of the circular neighborhood has to be defined carefully with respect to the degree of the intensity inhomogeneities. For images with high degree of intensity inhomogeneities, small scale parameters should be used. Unfortunately, the level set is less robust to initialization with small scale parameter than with larger one.

As an example of local region-based level set, in "C. Li, C. Kao, J. Gore, and Z. Ding, Minimization of Region-Scalable Fitting Energy for Image Segmentation, *IEEE Trans Image Process*. 2008 October; 17(10): 1940-1949", Li et al. compute local mean intensity inside a local neighborhood. In some extent, this local region-based level set is able to deal with intensity homogeneity. However, for some images with severe intensity homogeneity, as in the case of CT or MRI imagery, segmentation may lead to unsatisfactory results and require an intensity inhomogeneity correction as preprocessing.

An improved approach was proposed by the same team of researchers by following the seminal work of Mumford and Shah in "D. Mumford & J. Shah (1989), Optimal Approximations by Piecewise Smooth Functions and Associated Variational Problems, *Communications on Pure and Applied Mathematics*, XLII(5): 577-685." who have restated image segmentation methods as a functional minimization in order to compute optimal approximations of the original image to be segmented by a piecewise smooth function.

Therefore, Li et al. in "C. Li, R. Huang, Z. Ding, C. Gatenby, D. N. Metaxas, and J. C. Gore, A Level Set Method for Image Segmentation in the Presence of Intensity Inhomogeneities with Application to MRI, *IEEE Trans. Image Processing*, vol. 20 (7), pp. 2007-2016, 2011", model an acquired image as:

$$I=bJ+n \qquad (1)$$

which describes real-world image model with intensity inhomogeneity, where b, referred to as bias field, corresponds to the intensity inhomogeneity, J being the true image and n an additive noise.

Instead of computing a local mean intensity as a local region descriptor, in "C. Li, R. Huang, Z. Ding, C. Gatenby, D. N. Metaxas, and J. C. Gore, A Level Set Method for Image Segmentation in the Presence of Intensity Inhomogeneities with Application to MRI, *IEEE Trans. Image Processing*, vol. 20 (7), pp. 2007-2016, 2011", Li et al. proposed a region-based level set which is based on a local clustering of the image intensities within a local neighborhood, the image intensities being modeled by Equation (1). A local cluster center from a Gaussian distribution of the local intensities is then computed instead of a local mean intensity. Compared to other local region-based level sets, this approach is robust with respect to the intensity inhomogeneity as it incorporates this information in the model.

Edge-based level set models can be applied to images with intensity inhomogeneity as they rely only on the gradients in the image and include edge detector dependent terms in the functional. The aim of this approach is to attract the contour towards the boundaries of the structure to be segmented and to stop the evolution of the level set once the desired object edges are obtained. One example of edge-based level set is proposed in "C. Li, C. Xu, C. Gui, and M. D. Fox, "Distance Regularized Level Set Evolution and its Application to Image Segmentation", IEEE Trans. Image Processing, vol. 19 (12), pp. 3243-3254, 2010".

However, there are at least two drawbacks of this approach. First, when the images are too noisy, as this is the case for most medical imaging data, the contour can be attracted by local minimum and the level set can produce unwanted results. Second, when the objects to be detected have weak boundaries, the contour may continue to evolve outside the structure to be detected and produce boundary leakage problems. Therefore, those techniques are effective for images with salient and well-defined boundaries. In addition, edge-based level sets are known to be very sensitive to the initial conditions, i.e. the initial level set function.

In the case of bone segmentation and due to the nature of the images, especially in CT imagery with inhomogeneous intensities, small bone inter-gap (or interstitial distance), weak boundaries, high degree of noise, local region-based level sets are definitely appropriate. However, for bone segmentation, the minimum inter-bone gap must also be taken into account in addition to the degree of intensity inhomogeneities while choosing the appropriate scale parameter.

As the bone inter-gap is small, a small local neighborhood must be used in order to be able to locally segment very close bones, which requires a small scale parameter for all the images. Moreover, when the intensity inhomogeneities are high, a small scale parameter should also be chosen. However, there are drawbacks to using small scale parameters as they yield more edges and tend to produce segmented images with high background noise. Therefore, the iteration number of the level set must be set high enough in order to get rid of these unwanted pixels, which may increase considerably the processing time. Furthermore, the initialization must be close enough to the anatomical bone boundaries because, as mentioned above, edge-based level set and local region-based level set with a small scale parameter are very sensitive to the initial conditions.

It was found that local edge-based terms can be added to the local region-based terms to improve the local region-based level set, as proposed by Li et al. in "C. Li, R. Huang, Z. Ding, C. Gatenby, D. N. Metaxas, and J. C. Gore, A Level Set Method for Image Segmentation in the Presence of Intensity Inhomogeneities with Application to MRI, *IEEE Trans. Image Processing*, vol. 20 (7), pp. 2007-2016, 2011". It was found that these new additional local edge terms allow the level set to converge rapidly and be attracted to boundaries with high gradient intensity, i.e. boundaries of bones. Thus, the processing times are lower and the noise in the background are more efficiently suppressed.

The association of the local region-based terms and local edge-based terms is referred to as multiphase local-based hybrid level set, wherein the term 'multiphase' refers to the case where more than two regions have to be segmented. When only two phases are involved in order to segment two disjoint regions, i.e., the bone regions, as foreground, and the background region, the level set is referred to as two-phase local-based hybrid level set.

The multiphase local-based hybrid level set segmentation is based on the minimization of an energy functional which depends on both region and edge data, as described above. It has been found suitable to segment bones with weak or fuzzy boundaries, to segment close bones when their inter-bone gap is extremely narrow or even disappears, and to segment images with high degree of intensity inhomogeneity. An embodiment of the energy functional is provided below in Equation (2).

The balance of the edge-based term and the region-based term, represented by a parameter $\lambda$ in the following equations, has to be defined for the whole imaging data.

As mentioned above, the initialization must be close enough to the anatomical bone boundaries because the hybrid level set is very sensitive to the initial conditions. To deal with the initialization sensitivity of the hybrid level set, the binary masks, obtained with the 3D adaptive thresholding processing 22, are used to initialize the multiphase local-based hybrid level set function. It has been found that the association of local and global pixel intensity thresholds in the 3D adaptive thresholding processing 22, described above, provides binary masks with contours close to the anatomical bone boundaries, which is a desired property of initial conditions for the hybrid level set.

The multiphase hybrid level set segmentation is local since the intensities clustering and the edge detector function are computed inside a local circular neighborhood centered at each point of the filtered grayscale ROIs. Their values change dynamically over the image with respect to the position of the center of the neighborhood. The local circular neighborhood is defined by means of a Gaussian kernel, whose size is defined by a parameter, referred to as the scale parameter. It depends essentially on the minimum inter-bone gap for the whole imaging data and on the severity of the intensity inhomogeneities. This is a desired property for a narrow joint area (or inter-bone gap or interstitial distance) between two or more too close neighboring bones and for greyscale images with severe intensity inhomogeneities.

In an embodiment, a single scale parameter is used within all the ROIs in the primary image data and it does not change from one ROI to another, nor inside a single ROI.

Figure 5A:
FIGS. 5A, 5B, and 5C show an image of bones of an ankle.
Figure 5B:
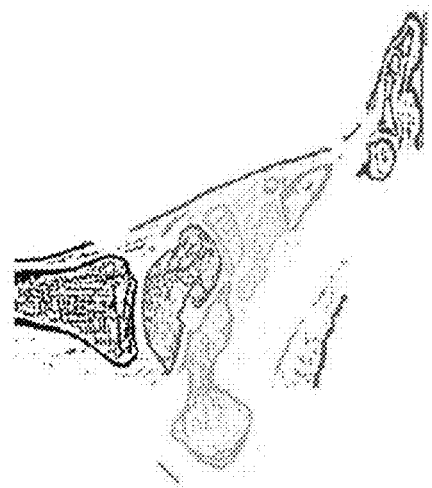
Figure 5C:
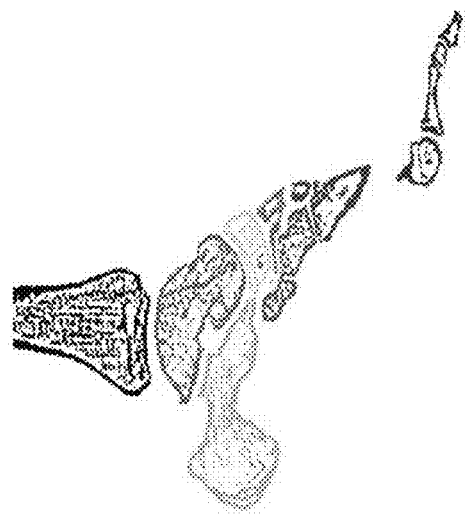

In an embodiment, the multiphase local-based hybrid level set segmentation is performed on each one of the ROIs of each one of the 2D images of the primary image data. As mentioned above, in an embodiment, the first purpose of the binary masks is to define ROIs in the 2D greyscale images and to hide everything except the inner section delimited by each one of them. As shown in FIGS. 5A and 5B, partial masking of the ROIs with the binary masks eliminates the bone-free area and lower noise. FIG. 5A shows an original grayscale image to be segmented. FIG. 5B shows the result of the multiphase local-based hybrid level set segmentation on the greyscale image in FIG. 5A without applying binary masks. Finally, FIG. 5C shows the whole segmented image following the multiphase local-based hybrid level set segmentation with application of binary masks. FIG. 5C illustrates the third purpose of the binary masks as reducing considerably the remaining background noise after the multiphase level set segmentation. For FIGS. 5B and 5C, as the multiphase local-based hybrid level set segmentation is applied on the ROIs of the image, each whole segmented image is obtained after merging all the segmented ROIs of the image.

As shown in FIGS. 5B and 5C, since application of the binary masks hides everything, except the inner section delimited by each one of them, the multiphase local-based hybrid level set segmentation is applied on each of the grayscale ROIs of the primary image data, following application of the binary masks obtained by 3D adaptive thresholding processing.

As level set segmentation is very time-consuming, partial masking of the grayscale images of the primary image data reduces the processing time, the noise, and other tissues that may be segmented in the background, the multiphase local-based hybrid level set segmentation being only applied on the grayscale ROIs whose sizes are much reduced compared to the whole image size.

Even though in the embodiment described herein, the multiphase local-based hybrid level set segmentation is applied on ROIs, it is appreciated that, in an alternative embodiment, it can be applied on the entire greyscale image.

As a region-based level set segmentation with a smaller scale parameter may yield a segmented image with more background noise than a larger one, the additional edge terms allow the level set to converge rapidly and be attracted to boundaries with high gradient intensity, i.e. boundaries of bones.

The multiphase local-based hybrid level set segmentation performs a partition of a ROI which includes regions belonging to more than one bone, in multiple blobs (or segments), each corresponding to one or more bones. The partition of the ROI is performed according to a set of image data such as and without being limitative, image intensity, intensity gradient, curvature or the like, and generates the secondary segmented image data including a 3D volume generated from a plurality of 2D images with segmented blobs. Additional image data such as texture and/or shape of the contour can be included in the level set algorithm. Texture can include applying constraints regarding the pixels inside the ROI while shape can include applying continuity and curvature constraints on the contour.

Figure 6:
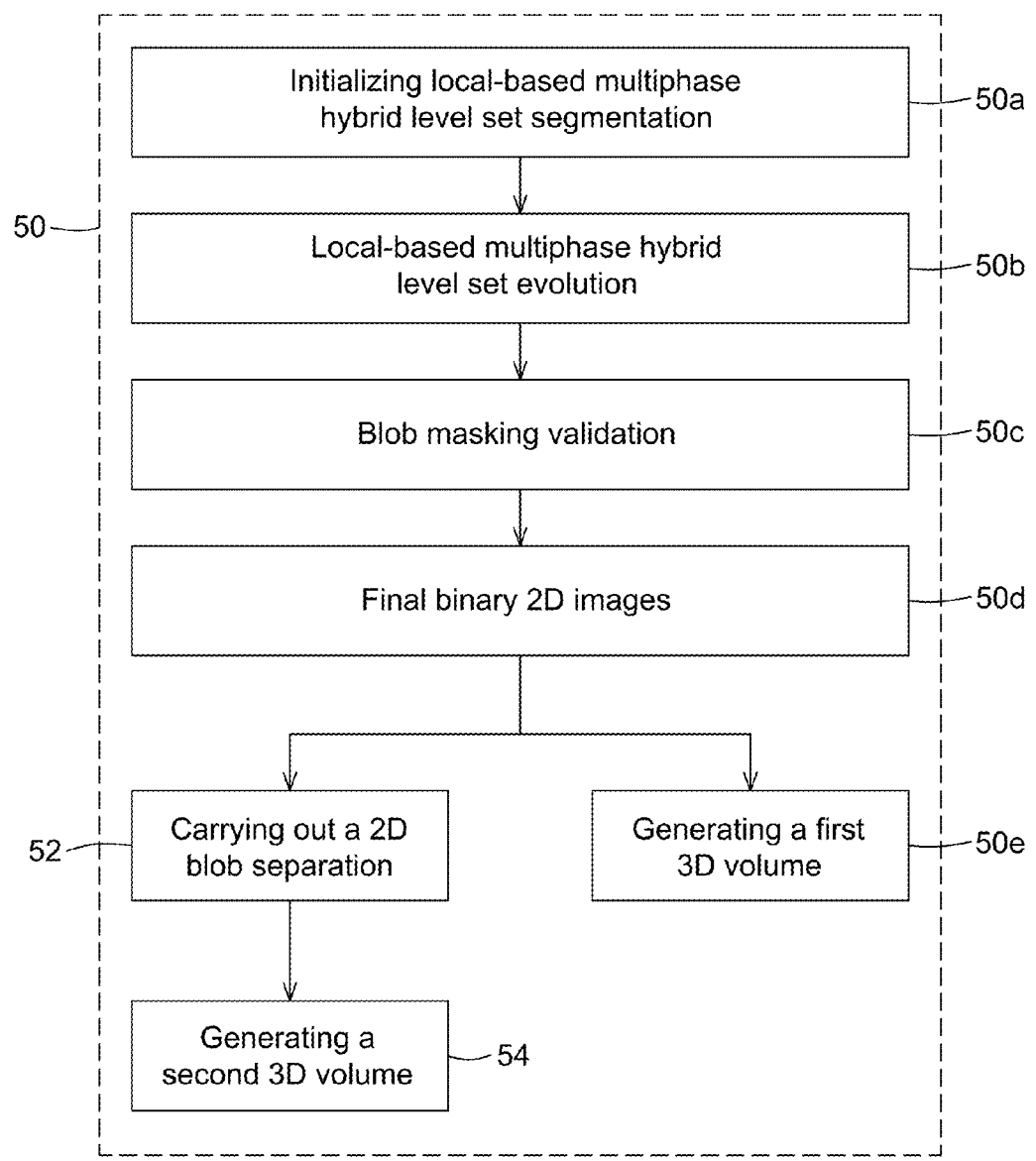
FIG. 6 is a flowchart of sequential steps of the multi-bone segmentation process for performing multi-bone segmentation in imaging data according to FIG. 1, in accordance with an embodiment.

In reference to FIG. 6, more detailed steps of the multi-bone segmentation 50 will now be described. In step 50*a*, the multiphase local-based hybrid level set is first initialized. As mentioned above, in an embodiment, each binary mask, obtained from the 3D adaptive thresholding processing, is used for the initialisation of the level set on each grayscale ROI which corresponds to the second purpose of the binary masks. In an embodiment, as mentioned above, instead of carrying out the level set on the whole image, the level set method is performed solely on the ROIs to reduce the processing time and the noise in the background of the whole images. However, in alternative embodiment, it can be performed on the entire greyscale image.

Then, in step 50b, the evolution of the multiphase local-based hybrid level set is performed. In the following, equations for a two-phase local-based hybrid level set, i.e. for segmenting two regions known as foreground and background, are given. In an embodiment, the energy functional for a two-phase model, in Equation (2) below, is to be minimized:

$$\mathcal{F}_{2\text{-}phase}(\phi,c,b) = (1-\lambda)\mathcal{E}_{region}(\phi,c,b) + \lambda\mathcal{E}_{edge}(\phi) + \mu\mathcal{R}_p(\phi) \quad (2)$$

where $\lambda$ is a positive constant that balances the contribution of the region-based terms and the edge-based terms ($0 < \lambda < 1$), $\phi$ being the level set function for a two-phase model, a phase corresponding to a region, b being the bias field accounting for the intensity inhomogeneity, and c being a vector representing intensity-based constant values in disjoint regions. The parameters b and c are further described in Li et al. in "C. Li, R. Huang, Z. Ding, C. Gatenby, D. N. Metaxas, and J. C. Gore, A Level Set Method for Image Segmentation in the Presence of Intensity Inhomogeneities with Application to MRI, *IEEE Trans. Image Processing*, vol. 20 (7), pp. 2007-2016, 2011".

In an embodiment, a relatively low value of $\lambda$, for instance and without being limitative smaller than 0.5, can be selected for imaging data characterized by weak boundaries, so as to privilege local-based region terms over local-based edge terms. In an embodiment, if the imaging data are relatively noisy with strong bone boundaries, a relatively high value of $\lambda$, for instance and without being limitative higher than 0.5, can be selected in order to privilege local-based edge terms. This can be combined with a relatively high scale parameter in order to get rid of local minima introduced by the noise.

For the region-based terms, in the embodiment below, the model based on local clustering criterion proposed by Li et al. in "C. Li, R. Huang, Z. Ding, C. Gatenby, D. N. Metaxas, and J. C. Gore, A Level Set Method for Image Segmentation in the Presence of Intensity Inhomogeneities with Application to MRI, *IEEE Trans. Image Processing*, vol. 20 (7), pp. 2007-2016, 2011". was followed with:

$$\mathcal{E}_{region}(\phi,c,b) = \int(\Sigma_{i=1}^{N}\int K_\sigma(y-x)|I(x)-b(y)c_i|^2 dy)\mathcal{M}_i(\phi(x))dx \quad (3)$$

with $K_\sigma$, a kernel function computed by means of a truncated Gaussian function of standard deviation $\sigma$, referred to as the scale parameter, $\rho$ being the radius of the circular neighborhood:

$$K_\sigma(u) = \begin{cases} \frac{1}{a}e^{-|u|^2/2\sigma^2}, & |u| \le \rho \\ 0, & \text{otherwise} \end{cases}$$

$\mathcal{M}_i$ is a membership function of each region $\Omega_i$, and is defined as:

$$\mathcal{M}_1(\phi) = \mathcal{H}_\epsilon(\phi)$$

$$\mathcal{M}_2(\phi) = 1 - \mathcal{H}_\epsilon(\phi)$$

$\mathcal{H}_\epsilon$ is the Heaviside function and is defined as:

$$H_\epsilon(\phi) = \frac{1}{2}\left[1 + \frac{2}{\pi}\arctan\left(\frac{\phi}{\epsilon}\right)\right]$$

depending on the parameter $\Sigma$.

The multiphase local-based hybrid level set introduces a new local-based edge term, as follows:

$$\mathcal{E}_{edge}(\phi) = \nu\mathcal{L}_g(\phi) + \alpha\mathcal{A}_g(\phi) \quad (5)$$

$\nu$ and $\alpha$ are normalization constants.

Where:

$$\mathcal{L}_g(\phi) \triangleq \int g_{\sigma,\tau}\delta_\epsilon(\phi)|\nabla\phi|dx \quad (6)$$

is the weighted length which computes the line integral over each piecewise smooth curves inside each local neighborhood which size is depending on $\sigma$, and adds them up for the whole image or the ROI. $\delta_\epsilon(\phi)$ is a derivative of the Heaviside function $\mathcal{H}_\epsilon$.

$$\mathcal{A}_g(\phi) \triangleq \int g_{\sigma,\tau}\mathcal{H}_\epsilon(-\phi)dx \quad (7)$$

is the weighted area of the region.

A local-based edge indicator function $g_{\sigma,\tau}$ is used as the weight of the two terms. These two local-based edge dependent terms are minimized when the curve is on object boundaries. The local-based edge indicator function $g_{\sigma,\tau}$ is defined as follows:

$$g_{\sigma,\tau} \triangleq \frac{1}{1+f_{\sigma,\tau}} \quad (8)$$

Where $f_{\sigma,\tau}$ is a local-based edge function defined as:

$$f_{\sigma,\tau}(x) = \int K_\sigma(y-x)u_\tau(y)dy \quad (9)$$

$u_\tau$ is the magnitude of image gradient:

$$u_\tau \triangleq |\nabla G_\tau * I|^2 \quad (10)$$

$G_\tau$ being a Gaussian kernel with a standard definition $\tau$ and I being the greyscale image.

$\mathcal{R}_p$ is the distance regularization term, as proposed by Li et al. in "C. Li, C. Xu, C. Gui, and M. D. Fox. Distance Regularized Level Set Evolution and its Application to Image Segmentation, *IEEE Trans. Image Processing*, vol. 19 (12), pp. 3243-3254, 2010" and defined as:

$$\mathcal{R}_p(\phi) = \int p(|\nabla\phi|)dx \quad (11)$$

The segmentation results are obtained through the minimization of the hybrid energy functional $\mathcal{F}$ by gradient descent method:

$$\frac{\partial\phi}{\partial t} = -\frac{\partial F_{2\,phase}}{\partial\phi} \quad (12)$$

Which gives:

$$\frac{\partial\phi}{\partial t} = -(1-\lambda)\delta_\epsilon(\phi)(e_1 - e_2) + \lambda\left(\nu\delta_\epsilon(\phi)div\left(g_{\sigma,\tau}\frac{\nabla\phi}{\|\nabla\phi\|}\right) + \alpha\,g_{\sigma,\tau}\,\delta(\phi)\right) + \mu div(d_p(|\nabla\phi|)\nabla\phi) \quad (13)$$

With:

$$e_i(x) = \int K_\sigma(y-x)|I(x) - b(y)c_i|^2\,dy, i = 1, 2 \quad (14)$$

i=1 for the first region and i=2 for the second region.

$\delta_\epsilon$ is the derivative of the Heaviside function $\mathcal{H}_\epsilon$ and depends also on $\epsilon$:

$$H_\varepsilon(\phi) = \frac{1}{2}\left[1 + \frac{2}{\pi}\arctan\left(\frac{\phi}{\varepsilon}\right)\right] \quad (15)$$

$$\delta_\varepsilon(\phi) = H'\varepsilon(\phi) = \frac{1}{\pi}\frac{\varepsilon}{\varepsilon^2 + \phi^2} \quad (16)$$

The last term of (13) corresponds to the regularization term $\mathcal{R}_p(\phi)$, $\mu$ is a positive constant.
The level set is initialized by:

$$\phi_0(x) = \begin{cases} -c_0, & \text{if } x \text{ is inside the mask} \\ c_0, & \text{otherwise} \end{cases} \quad (17)$$

where $c_0$ is a constant.

For the multiphase local-based hybrid level set, i.e. for segmenting more than two regions or two phases, the energy functional to be minimized is:

$$\mathcal{F}_{multiphase}(\Phi,c,b) = (1-\lambda)\mathcal{E}_{region}(\Phi,c,b) + \lambda\mathcal{E}_{edge}(\Phi) + \mu\mathcal{R}_p(\Phi) \quad (18)$$

Where $\Phi$ is a vector formed by k level set functions $\phi_i$, i=1 ... k for k regions or phases.

$$\Phi = (\phi_1(y), \ldots, \phi_k(y))$$

The number of the level set functions to be used is at least equal to:

$$k = \log_2(\mathcal{N})$$

where $\log_2$ is the logarithm to the base 2, N is the number of the regions to be segmented in the image.

For instance, in order to segment an image with four regions, i.e. N=4, at least two level set functions are used in the proposed multiphase local-based hybrid level set.

$\lambda$ is still a positive constant that balances the contribution of the region-based terms and the edge-based terms (0<$\lambda$<1).

For the region-based terms in the multiphase local-based hybrid level set, Li et al. in "C. Li, R. Huang, Z. Ding, C. Gatenby, D. N. Metaxas, and J. C. Gore, A Level Set Method for Image Segmentation in the Presence of Intensity Inhomogeneities with Application to MRI, IEEE Trans. Image Processing, vol. 20 (7), pp. 2007-2016, 2011" was followed:

$$\mathcal{E}_{region}(\Phi,c,b) = \int \Sigma_{i=1}^N e_i(x)M_i(\Phi(x))dx \quad (19)$$

where $e_i(x)$ is given by (14).

$$M_i(\Phi) = M_i(\phi_1(y), \ldots, \phi_k(y)) = \begin{cases} 1, & y \in \Omega_i \\ 0, & \text{else} \end{cases}$$

$\Omega_i$ being the region i.

The edge-based terms in the multiphase local-based hybrid level set are:

$$\mathcal{E}_{edge}(\Phi) = v\mathcal{L}_g(\Phi) + \alpha\mathcal{A}_g(\Phi) \quad (20)$$

Where:

$$\mathcal{L}_g(\Phi) = \Sigma_{j=1}^k \mathcal{L}_g(\phi_j) \quad (21)$$

$$\mathcal{A}_g(\Phi) = \Sigma_{j=1}^k \mathcal{A}_g(\phi_j) \quad (22)$$

With $\mathcal{L}_g(\phi_j)$ and $\mathcal{A}_g(\phi_j)$ being the new local-based edge terms in (6) and (7).

The segmentation results are obtained through the minimization of the multiphase hybrid energy functional $\mathcal{F}_{multiphase}$ by gradient descent method:

$$\frac{\partial \phi_1}{\partial t} = -\frac{\partial F_{multiphase}(\Phi)}{\partial \phi_1}, \ldots, \frac{\partial \phi_k}{\partial t} = -\frac{\partial F_{multiphase}(\Phi)}{\partial \phi_k} \quad (23)$$

which gives:

$$\frac{\partial \phi_1}{\partial t} = -(1-\lambda)\left(\Sigma_{i=1}^N \frac{\partial M_i(\Phi)}{\partial \phi_1}e_i\right) + \quad (24)$$
$$\lambda\left(v\delta_\varepsilon(\phi_1)div\left(g_{\sigma,\tau}\frac{\nabla\phi_1}{\|\nabla\phi_1\|}\right) + \alpha g_{\sigma,\tau}\delta(\phi_1)\right) + \mu div(d_p(|\nabla\phi_1|)\nabla\phi_1)$$

$$\frac{\partial \phi_k}{\partial t} = -(1-\lambda)\left(\Sigma_{i=1}^N \frac{\partial M_i(\Phi)}{\partial \phi_k}e_i\right) + \quad (25)$$
$$\lambda\left(v\delta_\varepsilon(\phi_k)div\left(g_{\sigma,\tau}\frac{\nabla\phi_k}{\|\nabla\phi_k\|}\right) + \alpha g_{\sigma,\tau}\delta(\phi_k)\right) + \mu div(d_p(|\nabla\phi_k|)\nabla\phi_k)$$

For instance, for a four phase model with two level set functions $\phi_1$ and $\phi_2$, the membership functions $M_1$, $M_2$, $M_3$ and $M_4$ are expressed as:

$$M_1(\phi_1,\phi_2) = H_\epsilon(\phi_1)H_\epsilon(\phi_2)$$

$$M_2(\phi_1,\phi_2) = H_\epsilon(\phi_1)(1-H_\epsilon(\phi_2))$$

$$M_3(\phi_1,\phi_2) = (1-H_\epsilon(\phi_1))H_\epsilon(\phi_2)$$

$$M_4(\phi_1,\phi_2) = (1-H_\epsilon(\phi_1))(1-H_\epsilon(\phi_2))$$

For the multiphase local-based hybrid level set, including the two-phase local-based hybrid level set, the parameters are set empirically depending on the properties of the images to be segmented, including the type of images for the degree of intensity inhomogeneity (CT, MRI or other) and the minimum inter-gap distance of the anatomical bone region to be segmented (ankle, forefoot, hip, shoulder, and the like).

Figure 4A:
FIGS. 4A and 4B are greyscale images of bones of an ankle on which contours obtained by different level set segmentations have been applied.
Figure 4B:
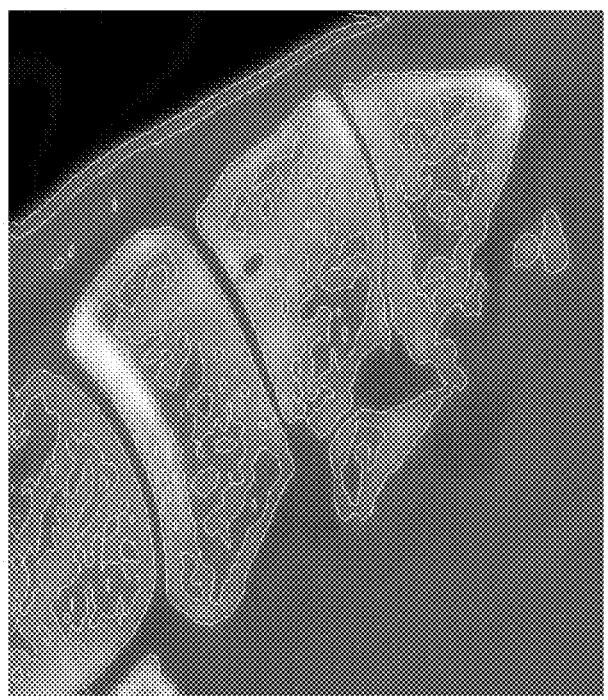

In order to compare the proposed multiphase local-based hybrid level set with the region-based level set described in "C. Li, R. Huang, Z. Ding, C. Gatenby, D. N. Metaxas, and J. C. Gore, A Level Set Method for Image Segmentation in the Presence of Intensity Inhomogeneities with Application to MRI, IEEE Trans. Image Processing, vol. 20 (7), pp. 2007-2016, 2011", the parameters were chosen so as to get almost similar foreground (i.e. bones) and background results. FIG. 4A shows the contour of the segmented blobs resulting from the region-based level set described in Li et al. (2011) applied on the original greyscale image. FIG. 4B shows the contour of the segmented blobs resulting from the multiphase local-based hybrid level set, described above, applied on the same original greyscale image. Experiments showed that hybrid-based level set processing time (FIG. 4B) is one third of the region-based level set processing time (FIG. 4A). Furthermore, the multiphase local-based hybrid level set produced segmented images with less background noise. This result is interesting for noisy images with high degree of intensity inhomogeneities like CT or MRI images and for images which need local-based segmentation requiring small scale parameter like images characterized by close bones.

As mentioned above, region-based level sets with small scale parameter and edge-based level sets are sensible to the initialization. As the proposed multiphase local-based hybrid level set operates with those two properties, it is also sensible to the initialization, as shown in FIGS. 7A to 7E, described in further details below. As mentioned above, the initialization should be close to the anatomical bone boundaries. Thus, each binary mask, obtained from the 3D adaptive thresholding processing, is used for the initialisation of the level set on each grayscale ROI. These binary masks have contours close to the anatomical bone boundaries.

Figure 7A:
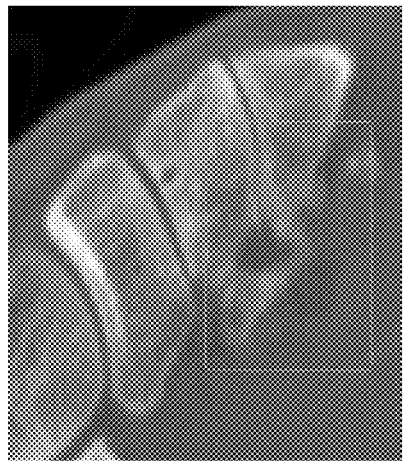
Figure 7B:
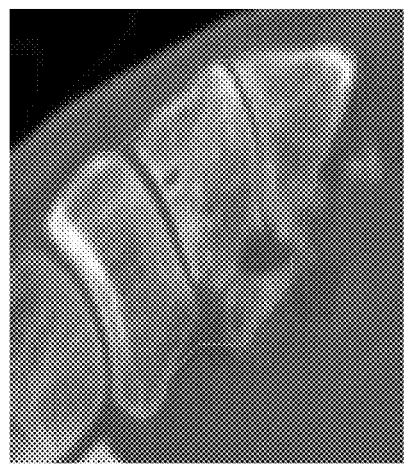
Figure 7C:
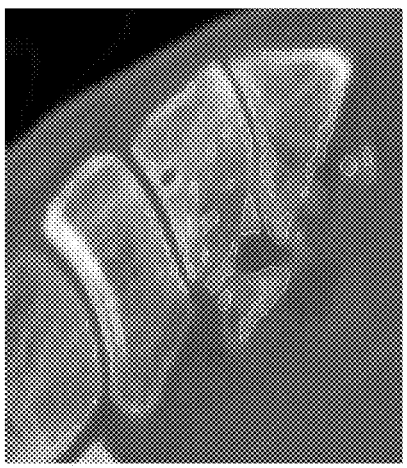
Figure 7D:
Figure 7E:
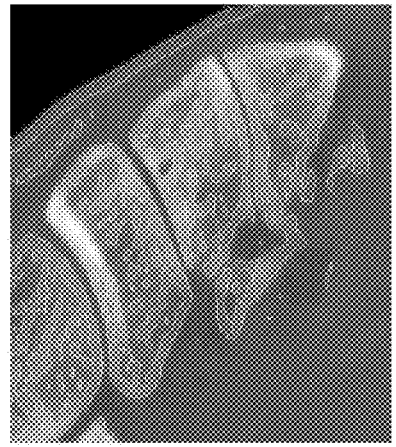

FIGS. 7A to 7E show the influence of the initialization of the multiphase local-based hybrid level set on the bone segmentation results. In the embodiment shown, the multiphase is two-phases: (a) the bones as foreground and (b) the background. FIG. 7A and FIG. 7B show the initialization of the multiphase local-based hybrid level set by an arbitrary rectangular contour and a mask respectively. FIG. 7C shows the segmentation results with the arbitrary rectangular contour shown in FIG. 7A and FIG. 7D shows the results with a mask shown in FIG. 7B. Both segmentations shown in FIGS. 7C and 7D have been obtained with the same set of parameters including the same iteration number. FIG. 7D shows that, with the same set of parameters, the initialization by the binary mask is more effective than with an arbitrary rectangular initialization. More particularly, all contours are closed and the background is almost noise free. FIG. 7E shows the results of the multiphase local-based hybrid level set with an arbitrary rectangular as initialization, similar to FIG. 7A. For this segmentation, the number of iterations had to be increased in order to obtain almost the same foreground as for FIG. 7D. Therefore, the processing time was more than three times longer than with mask initialization. Furthermore, the resulting contours are less closed with a higher background noise than for the segmentation result shown in FIG. 7D.

Thus, the sensitivity of the multiphase local-based hybrid level set to initial conditions due to a choice of a small value of scale parameter can be resolved by initializing the multiphase local-based hybrid level set by a contour close to anatomical bone boundaries, i.e. the boundaries of object to be segmented. Furthermore, the sensitivity of the edge terms of the multiphase local-based hybrid level set to initial conditions can also be resolved by initializing the multiphase local-based hybrid level set by a contour close to the anatomical bone boundaries.

Figure 6A:
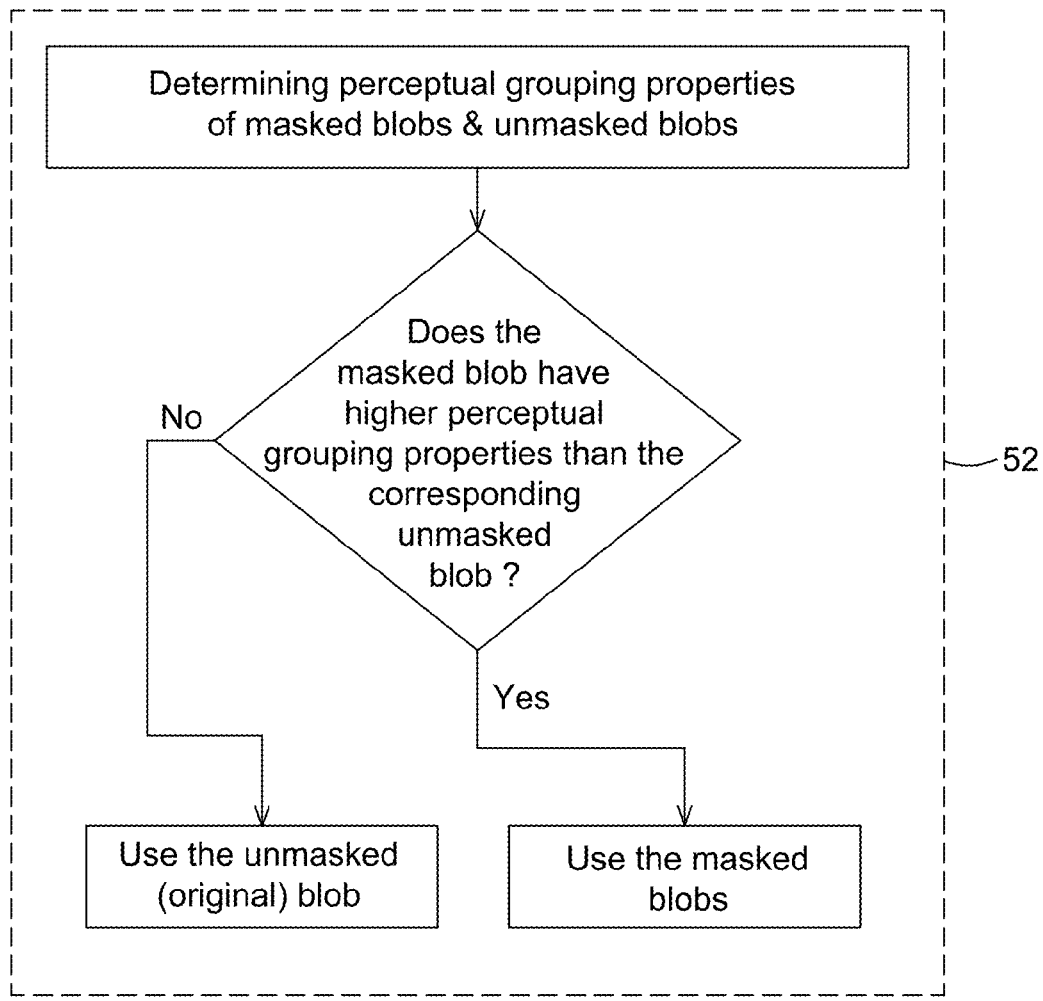
FIG. 6A is a flowchart of sequential steps of a blob masking validation of the multi-bone segmentation of FIG. 6, in accordance with an embodiment.

In the following, the segmented blobs obtained by the multiphase local-based hybrid level set segmentation 50b are referred to as original (or unmasked) blobs. To discard remaining background noise, a blob masking validation step 50c is carried out on each of these original blobs in order to determine the final segmented blob to be retained. More particularly, the binary masks, obtained with the 3D adaptive thresholding processing 22, are applied to the original (or unmasked) blobs, obtained following the multiphase local-based hybrid level set segmentation 50b. Thus, by masking the resulting binary subimages from the segmentation with the thresholded blobs, the background noise is substantially eliminated. Then, for each remaining blobs in the masked binary subimage, a blob matching with the unmasked blobs in the binary subimage, obtained following the segmentation, is carried out by means of blob labelling and area comparison. Only blobs which have a matching pair between masked and unmasked binary subimages are considered. Once each blob in the masked binary subimage is paired with a corresponding unmasked blob, the computation and the comparison of their perceptual grouping properties are determined and compared (FIG. 6A). In an embodiment, the perceptual grouping properties can include the smoothness, continuity, closure and solidity of a blob. A blob resulting from a proper segmentation should have a regular and smooth contour as acknowledged in Gestalt theories (smoothness, closure, solidity and good continuation).

For each pair of corresponding blobs, the blob having the highest perceptual grouping properties is retained as the final segmented blob for the following steps. For instance, if the smoothness of an unmasked (original) blob is higher than the smoothness of the corresponding masked blob, the original unmasked blob is selected as the final segmented blob, otherwise, the masked blob is retained as the final segmented blob.

Figure 8A:
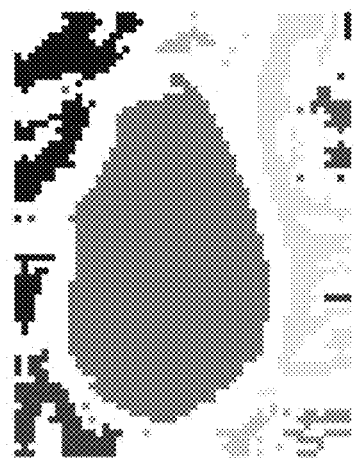
Figure 8B:
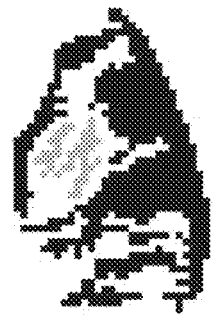
Figure 8C:
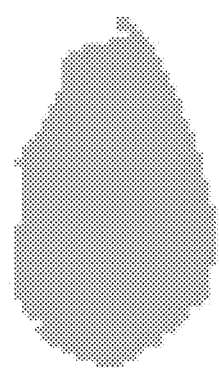

FIG. 8A shows the unmasked (original) blobs resulting from the multiphase local-based hybrid level set segmentation 50b where each one of the unmasked blob is labeled by a different grey tone. The blob masking 50c is then applied to this binary subimage in order to discard remaining background noise. FIG. 8B shows the same binary subimage following blob masking, i.e. the masked blobs. By visually comparing FIGS. 8A and 8B, for this particular blob, there is shown that the blob masking deteriorates the blob. Perceptual grouping properties are then computed for the masked blob (FIG. 8b) and for the corresponding unmasked (or original) blob (FIG. 8A). As expected from the visual comparison, the perceptual grouping properties of the unmasked blob (FIG. 8A) are higher than those of the masked blob (FIG. 8B), the unmasked blob is retained as the final segmented blob. The final segmented blob is shown in FIG. 8C. More particularly, FIG. 8C shows the final noise free background binary subimage with the selected segmented blob as stated in 50d.

Then, referring back to FIG. 6, in step 50d, a first set of secondary segmented imaging data including a plurality of binary images are generated. The first set of secondary images includes the final segmented blobs, i.e. the blobs following the blob masking validation 50C. It includes a combination of masked blobs and unmasked (original) blobs, i.e. the ones having the highest perceptual grouping properties.

Using the first set of secondary segmented imaging data, in step 50e, a first 3D volume is generated by stacking all secondary binary images obtained from step 50d. A 3D connected component analysis is applied to this 3D binary volume in order to get connected 3D binary subvolumes. The first 3D volume is stored in a memory of a processing unit performing the method or any other suitable support accessible by the processing unit for further use, as will be described in more details below.

It happens that two or more too close neighboring bones may not be separated through the multiphase local-based hybrid level set segmentation due to extremely narrow or non-existent gap between them. When two or more too close neighboring bones may not be separated through the multiphase local-based hybrid level set segmentation, a subsequent 2D bone separation 52 may then be performed, as will be described in further details in reference to FIG. 6A.

The 2D blob separation step is an optional step performed on the first set of secondary binary images in step 52 to generate a second 3D volume in step 54, as will be described in more details below.

Figure 9:
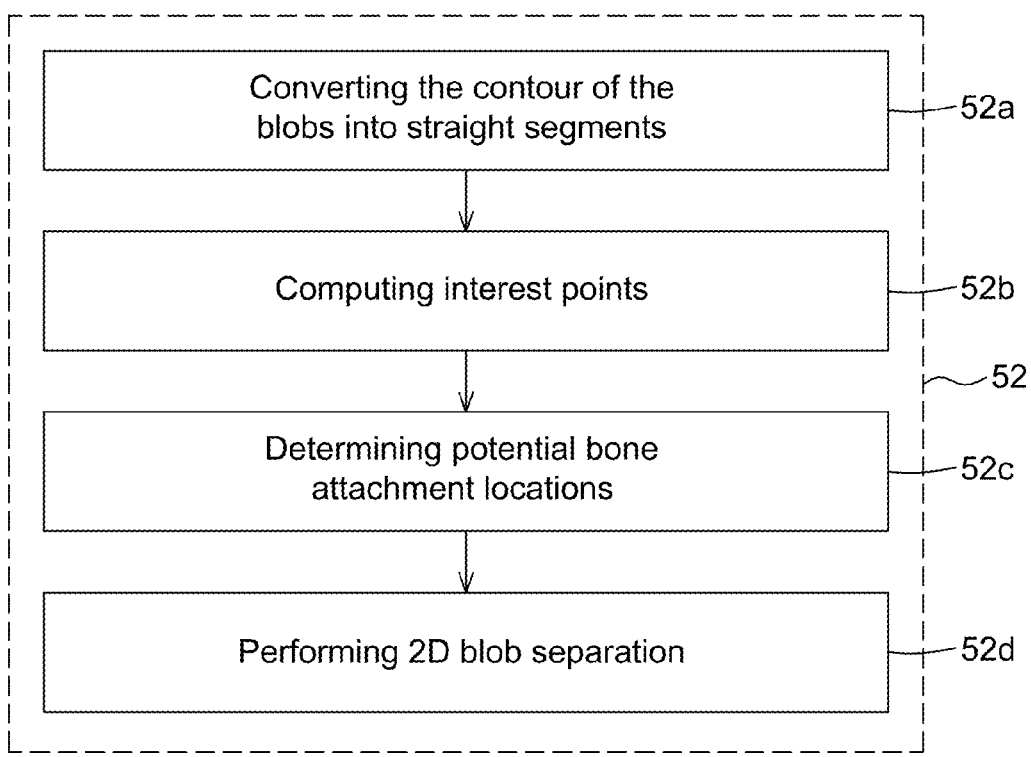
FIG. 9 is a flowchart of sequential steps of a 2D blob separation processing following the multiphase local-based hybrid level set segmentation of FIG. 6.

Step 52 is described in further details in reference to FIGS. 9 and 10. For each one of the binary images of the first set of secondary segmented imaging data, the contour of the segmented blobs, either the unmasked (original) blobs or the masked blobs, are converted into straight segments in step 52a as shown in FIG. 10A. More particularly, straight segments are created from the contours of the blobs. In FIG. 10A, the segmented blob shows that two bones are attached to each other. In fact, the talus bone and the navicular bone are attached following the multiphase local-based hybrid level set segmentation, at least because the segmented blob in this 2D binary subimage belongs to the two bones. Then, interest points are computed in step 52*b*. Interest points are identified based on a relevance measure ($K_{relevance}$) proposed by Latecki et al. "L. J. Latecki, R. Lakämper, Convexity Rule for Shape Decomposition Based on Discrete Contour Evolution, Computer Vision and Image Understanding (CVIU), vol. 73, pp. 441-454, 1999." based on the angle between two consecutive straight segments ($s_1$, $s_2$) and their lengths.

$$K_{relevance} = \frac{\beta(s_1, s_2)l(s_1)l(s_2)}{l(s_1) + l(s_2)}$$

β: angle between two consecutive segments $s_1$ and $s_2$
l($s_1$) and l($s_2$): lengths of two consecutive segments Then, using the computed interest points, locations for bone attachments are determined in step 52*c*. The interest points relevance measures are compared to a predetermined relevance threshold and the interest points meeting the predetermined relevance threshold are determined as being a bone attachment location. For each one of the bone attachment location, erosion will be carried out, as will be described in more details below.

Figure 10A:
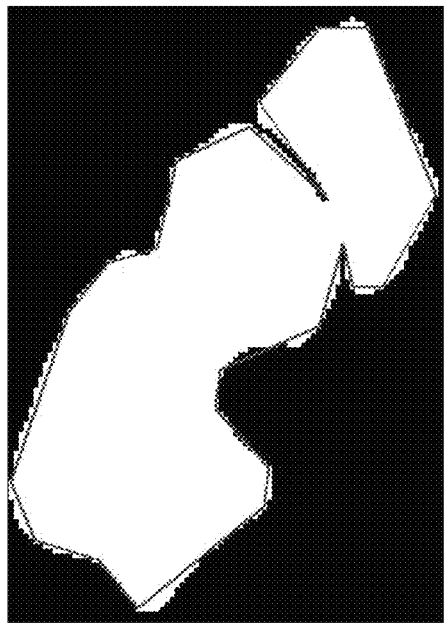
FIG. 10A is a binary image of a segmented blob having a bone attachment location defined by a pair of interest points, the generated straight segments being overlaid on the segmented blob.
Figure 10B:
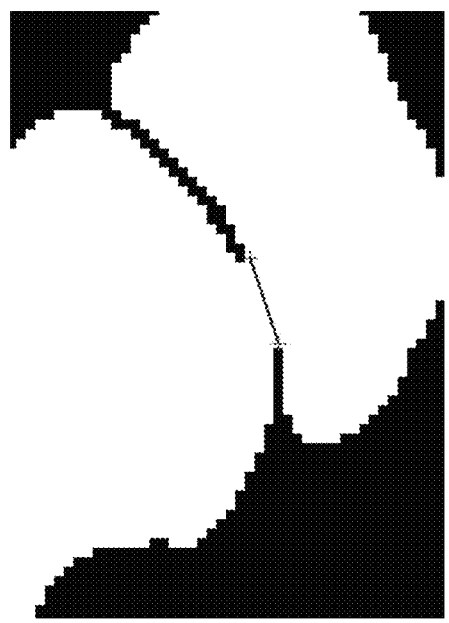
FIG. 10B is a section of the binary image of FIG. 10A, enlarged, with two detected interest points joined by a line.

Then, the interest points identified as being a bone attachment location are grouped in pairs and the distance separating two interest points of a pair is computed as shown in FIG. 10B wherein two interest points are joined by a line. Then, the computed distance is compared to a predetermined distance threshold. If the computed distance meets the predetermined distance threshold, i.e. for instance, if the computed distance is smaller than the predetermined distance threshold, the pair of interest points is determined as defining a linear bone attachment location. The other ones of the interest points identified as being a potential bone attachment are identified as being a punctual potential bone attachment location.

Figure 10C:
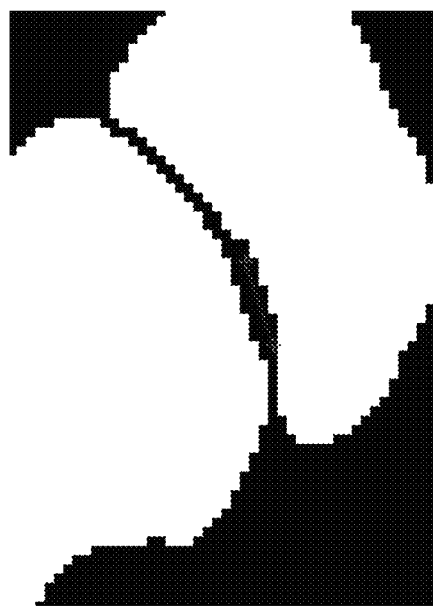
FIG. 10C is the binary image of FIG. 10B following bone separation by local erosion along the line.
Figure 10D:
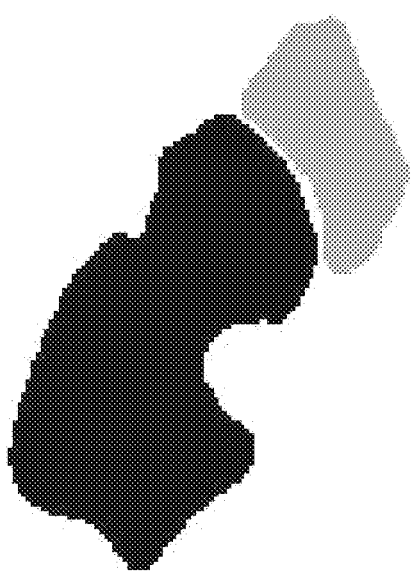
FIG. 10D is the binary image of FIG. 10A following bone separation by local erosion along the line.

Finally, in step 52*d*, for the bone attachment line(s) and point(s) determined in step 52*c*, a 2D blob separation is carried out. For a bone attachment line defined by a pair of interest points, a local rectangular erosion along the line linking the two points of interest is performed in order to separate the two potentially attached bones as shown in FIG. 10C. The erosion should be local to erode only the area wherein the two bones are attached. To perform a local erosion, a local mask, different from the binary masks obtained with the 3D adaptive thresholding processing 22, is applied to the 2D image along the bone attachment line in order to define a local neighborhood. In FIG. 10C, the local erosion was performed with a rectangular structuring element. The parameters of the structuring element for performing the local erosion and the local mask are defined based on the position, the distance and the angle defined by the pair of interest points. More specifically, the dimension and the orientation of the rectangular structuring element are defined by means of the location of the interest points. FIG. 10D shows the blobs resulting from the second 2D blob separation 52, i.e. wherein the talus bone and the navicular bone are segmented.

When bone attachment location is a bone attachment point (i.e. a punctual bone attachment location) defined by a single point of interest, i.e. two neighboring bones are attached to each other by one pixel, a local erosion with a square structural element is applied.

The above-described 2D blob separation is designed to be efficient when applied within a binary subimage in sagittal view where two bones are attached to each other, such as in the configuration on FIG. 10A.

Referring back to FIG. 7, following the 2D blob separation step 52, a second set of secondary segmented imaging data is obtained including a plurality of 2D binary images. Using the second set of secondary segmented imaging data, in step 54, a second 3D volume is generated by stacking all binary images obtained from step 52. The second 3D volume is stored in a memory of a processing unit performing the method or any other suitable support accessible by the processing unit for further use, as will be described in more details below.

Even though in the embodiment described below, the 2D blob separation is performed following a multiphase local-based hybrid segmentation, it is appreciated that it can be performed after any other suitable segmentation.

Figure 11:
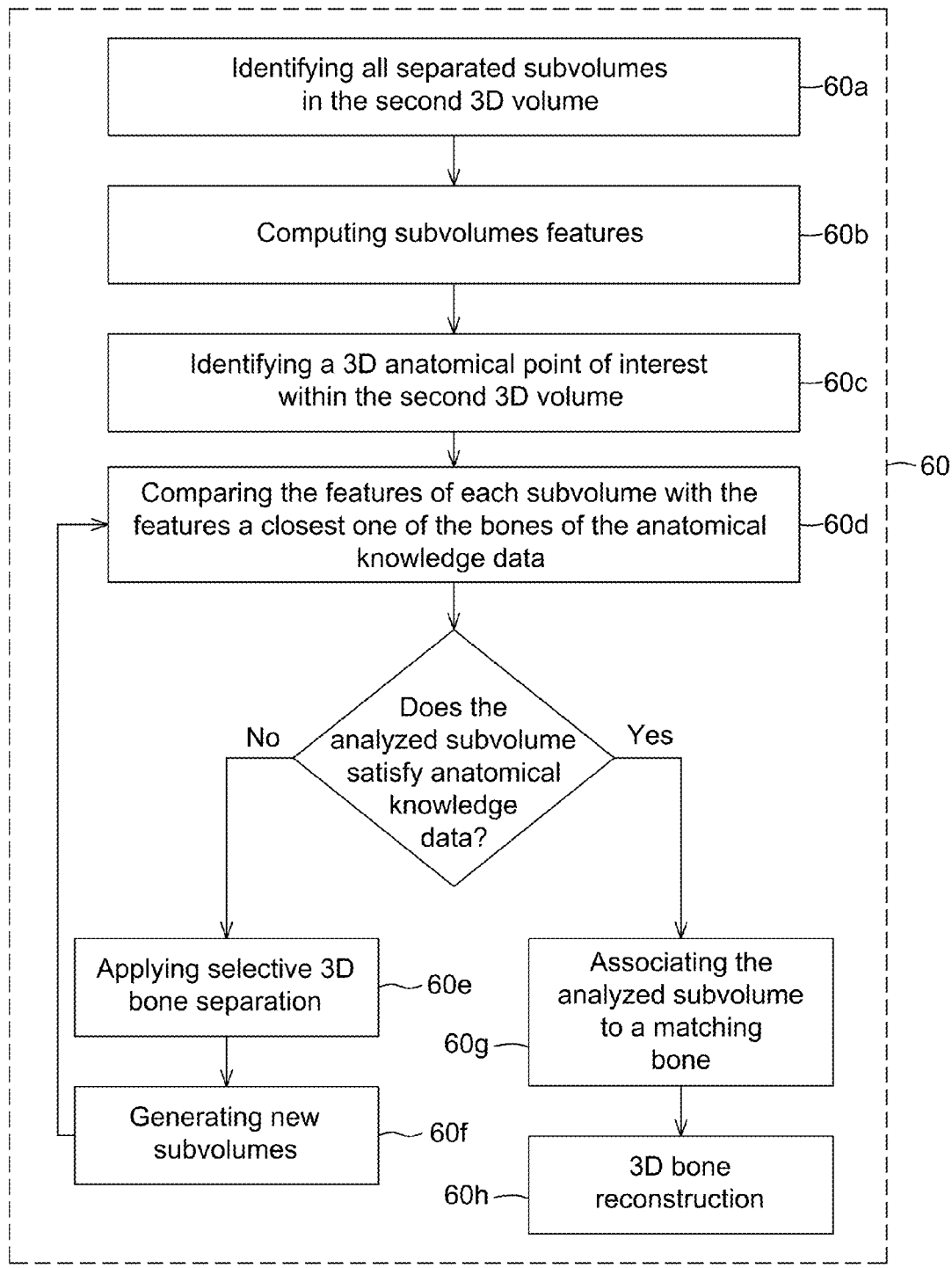
FIG. 11 is a flowchart of sequential steps of an anatomical component identification processing of the method for performing multi-bone segmentation in imaging data according to FIG. 1, in accordance with an embodiment.

Now referring to FIG. 11, a further step of the method 10 includes the identification of anatomical components 60, such as the bones, in the second 3D volume, i.e. the one obtained following step 52, using anatomical knowledge data relative to the section of the body structure of the corresponding imaging data.

In an embodiment, the step of identification of anatomical components 60 is performed based on anatomical knowledge data relative to the section of the body structure being analyzed, such as a foot, a hand, an ankle, a hip or the like. For example and without being limitative, the anatomical knowledge data can be stored in an anatomical knowledge data file, in a memory of a processing unit performing the method or any other suitable support accessible by the processing unit. The anatomical knowledge data includes general information regarding the specific body structure and geometry thereof, such as ranges of the relative lengths and volumes of the bones of the body structure, distances between the adjacent bones and the like. One skilled in the art will therefore understand that, in an embodiment, the anatomical knowledge data includes data relative to a plurality of body structures including bones which can be segmented using the present method, the appropriate body structure being selected according to the body structure being analyzed.

For identifying the anatomical components, the first step (step 60*a*) includes identifying in the second 3D volume, all separated 3D subvolumes by 3D connected component analysis. A subvolume corresponds to a respective one of the blobs, identified in the 2D binary images, combined with adjacent and corresponding ones of the blobs of other images in the 3D volume. Then, the features of the subvolumes are computed in step 60*b*. For instance and without being limitative, these features include the volume, length, 3D centroid, bounding box, and extreme 3D points.

A point of anatomical interest is then identified in the second 3D volume in step 60*c*. A point of anatomical interest can include, for example, the tip of the big toe for foot bone identification.

For each one of the subvolumes, starting from the point of anatomical interest, the features of the analyzed subvolume are compared to the features of the anatomical knowledge data in step 60*d*. The anatomical knowledge data include the features of each one of the bones that are included in the 3D volume being analyzed. More particularly, from the anatomical point of interest, a first one of the subvolumes is analyzed to be associated with one of the bones according to the anatomical knowledge data. This is achieved by proximity criteria and other anatomical features which can include and are not limited to extremity 3D points, centroid, length, volume, and axes. First, a closest one of the bones in the anatomical knowledge data is identified by proximity criteria. If the features of the subvolume being analyzed substantially correspond to the features of the anatomical knowledge data associated with the identified closest bone, the analyzed subvolume is associated to the respective bone (step 60g), i.e. the matching bone. For instance, if the features of the subvolume being analyzed substantially correspond to the features of the identified closest bone stored in the anatomical knowledge data, the subvolume is associated to the respective bone having substantially corresponding features.

In an embodiment, the bone identification processing is performed sequentially by proximity to a last one of associated 3D subvolumes, starting from the 3D subvolume closest to the 3D anatomical point of interest.

For example and without being limitative, if the body structure is a foot including a metatarsus, the anatomical knowledge data can include information such as its length. For instance, a mean length of a metatarsus can be about 6 cm (this value is determined a priori using anatomical statistical data or by supervised learning). If the identified closest bone for a subvolume to be identified is the metatarsus, a length of the subvolume is compared to the length of metatarsus stored in the anatomical knowledge data. If the subvolume to be identified has a 20 cm length, it is not associated to a metatarsus. As mentioned above, it is appreciated that the comparison criteria can be based on other features of the anatomical knowledge data than a length of the bone.

Then, if the features of the subvolume being analyzed do not correspond to the features of the identified closest one of the bones as described in the anatomical knowledge data and as exemplified above, a selective 3D bone separation step is performed in step 60e. Several criteria based on 3D features of the subvolume are evaluated before applying the selective 3D bone separation. For instance, the 3D bone separation can be carried out based on a ratio of the volume of the 3D blob and the volume of the bounding box including the 3D blob, i.e. a 3D solidity test is carried out. If the ratio is smaller than a bone separation threshold, the 3D bone separation is performed. It was found that attached and sparse 3D blobs, such as two attached metatarsus do not have a high "3D solidity" property, i.e. the ratio of the volume of the 3D blob and the volume of the bounding box including the 3D blob is relatively low. The criteria can also be based on the blob volume. The selective 3D bone separation is performed by a set of 3D morphological operations which may include 3D morphological erosion, opening, dilation and closing.

Following the selective 3D bone separation, new 3D subvolumes are generated in step 60f and the new 3D subvolumes are then sequentially compared to features of the anatomical knowledge data in step 60d. Once again, if the features of the subvolume being analyzed substantially correspond to the features of the anatomical knowledge data associated to an identified closest one of the bones, the subvolume being analyzed is associated to the respective bone (step 60g). Otherwise, a selective 3D bone separation step (step 60e) is performed as detailed above. The bone identification sequence can vary and be based on the body structure being modelized.

For each one of the subvolumes being associated to a respective bone, the 3D bone is reconstructed by a set of morphological operations including a morphological reconstruction in step 60h. These operations take into account the respective bone and the first 3D volume in order to restore accurately the original size and shape of the respective bone. This reconstruction step is performed since several morphological operations have been applied to each original binary image after the level set segmentation, including 2D and 3D bone separation.

Once the particular subvolume is associated to a respective one of the bones (step 60g) and reconstructed (step 60h), the particular subvolume is substracted from the second 3D volume. Successive bone searching and identification are performed if more than one bone is to be segmented. More particularly, successive bone searching and identification are performed for each one of the subvolumes of the second 3D volume.

Once all subvolumes have been associated to a bone of the bone structure and reconstructed, tertiary segmented image data are obtained. 3D models of the bones can be generated from the tertiary segmented image data. For instance, the software Geomagic™ can be used to create 3D bone models using 3D point clouds. The resulting 3D bone model, in which each one of the bones is identified, can be used in any subsequent task, such as for example the design of a cutting guide or an implant for a specific bone of the body structure or a joint thereof.

The designed cutting guide or/and implant can be manufactured with known methods such as and without being limitative 3D printing, laser sintering, molding, machining, or a combination thereof.

One skilled in the art will understand that, in an embodiment, a system for performing the multi-bone segmentation in imaging data, as described above, is also provided. The system includes a processing device with a processor coupled to a memory. The processing device includes an image preprocessing module, a multi-bone segmentation module including a multiphase local-based hybrid level set segmentation sub-module, and an anatomical component identification module stored on the memory and executable by the processor of the processing device. These modules interact together in order to provide the tertiary segmentation data from the imaging data.

The processing device is adapted to receive imaging data from an imaging apparatus (not shown), such as a CT scanner (or a processing device connected to the imaging apparatus), for example through a network, via a data storage device, or the like, and process the imaging data using the above mentioned modules in order to generate the tertiary segmentation data which can be used as data for generating the three-dimensional model.

For example, in an embodiment, the imaging data are received by the image preprocessing module and processed in accordance with the steps of the method described above and the flowcharts of FIGS. 2A and 2B, in order to generate the primary image data. The primary image data are received by the multi-bone segmentation module and are processed in accordance with the steps of the method described above in order to generate the secondary segmented data. The secondary segmented data are subsequently received by the anatomical component identification module and are processed according to the above described steps of the method and the flowcharts of FIG. 11 in order to associate each one of the subvolumes to a respective one of the bones and generate the tertiary segmented image data.

Several alternative embodiments and examples have been described and illustrated herein. The embodiments of the invention described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. It is understood that the invention may be embodied in other specific forms without departing from the central characteristics thereof. The present examples and embodiments, therefore, are to be considered in all respects as illustrative and not restrictive, and the invention is not to be limited to the details given herein. Accordingly, while specific embodiments have been illustrated and described, numerous modifications come to mind without significantly departing from the scope of the invention as defined in the appended claims.

The invention claimed is:

1. A computer implemented method for performing bone segmentation in imaging data of a section of a body structure, the method comprising:
Using a processor,
Obtaining the imaging data including a plurality of 2D images of the section of the body structure; and
Performing a multiphase local-based hybrid level set segmentation on at least a subset of the plurality of 2D images by minimizing an energy functional including a local-based edge term and a local-based region term computed locally inside a local neighborhood centered at each pixel of each one of the 2D images on which the multiphase local-based hybrid level set segmentation is performed, the local neighborhood being defined by a Gaussian kernel whose size is determined by a scale parameter ($\sigma$);
Generating a 3D volume including a plurality of 3D subvolumes from the segmented blobs of the secondary segmented image data; and
Associating an anatomical component to each one of the 3D subvolumes using the anatomical knowledge data relative to the
section of the body structure of the imaging data.

2. The computer implemented method of claim 1, wherein the local neighborhood is circular and performing the multiphase local-based hybrid level set segmentation further comprises: for each pixel of the 2D images, dynamically changing region descriptors based on a position of a center of the local neighborhood.

3. The computer implemented method of claim 1, further comprising: selecting a value of $\lambda$ to adjust a performance of the multiphase local-based hybrid level set segmentation with $\lambda$ being greater than 0 and smaller than 1, wherein $\lambda$ multiplies the local-based edge term and (1−$\lambda$) multiplies local-based region term.

4. The computer implemented method of of claim 1, wherein the 2D images include two phases and the energy functional is:

$$\mathcal{F}_{2\text{-}phase}(\phi,c,b) = (1-\lambda)\mathcal{E}_{region}(\phi,c,b) + \lambda \mathcal{E}_{edge}(\phi) + \mu \mathcal{R}_p(\phi)$$

where $\lambda$ is greater than or equal to 0 and smaller than or equal to 1, $\mu$ is a positive constant, b is a bias field accounting for intensity inhomogeneity, and c is a vector representing intensity-based constant values in disjoint regions, $$\mathcal{E}_{edge}(\phi) = \nu \mathcal{L}_g(\phi) + \alpha \mathcal{A}_g(\phi)$$

wherein $\nu$ and $\alpha$ are normalization constants, $$\mathcal{L}_g(\phi) \triangleq \int g_{\sigma,\tau}\, \delta_\varepsilon(\phi)|\nabla \phi| dx,$$

$$\mathcal{A}_g(\phi) \triangleq \int g_{\sigma,\tau}\, \mathcal{H}_\varepsilon(-\phi) dx,$$

$$g_{\sigma,\tau} \triangleq \frac{1}{1+f_{\sigma,\tau}},$$

$$f_{\sigma,\tau}(x) = \int K_\sigma(y-x) u_\tau(y) dy,$$

$$u_\tau \triangleq |\nabla G_\tau * I|^2$$

with $G_\tau$ being a Gaussian kernel with a standard definition $\tau$ and I being the image, $K_\sigma$, a kernel function computed by means of a truncated Gaussian function of the scale parameter ($\sigma$), $\rho$ being the radius of the local circular neighborhood:

$$K_\sigma(u) = \begin{cases} \frac{1}{a} e^{-|u|^2/2\sigma^2}, & |u| \leq \rho \\ 0, & \text{otherwise} \end{cases}$$

and $$H_\varepsilon(\phi) = \frac{1}{2}\left[1 + \frac{2}{\pi}\arctan\left(\frac{\phi}{\varepsilon}\right)\right]$$

with $\varepsilon$ being a parameter; and $$\mathcal{E}_{region}(\phi,c,b) = \int (\Sigma_{i=1}^N \int K_\sigma(y-x)|I(x)-b(y)c_i|^2 dy)\mathcal{M}_i(\phi(x)) dx$$

$\mathcal{M}_i$ is a membership function of each region $\Omega_i$, and is defined as:

$$\mathcal{M}_1(\phi) = \mathcal{H}_\varepsilon(\phi)$$

$$\mathcal{M}_2(\phi) = 1 - \mathcal{H}_\varepsilon(\phi)$$

wherein $\mathcal{R}_p$ is a regularisation term:

$$\mathcal{R}_p(\phi) = \int p(|\nabla \phi|) dx$$

and the minimization of the hybrid energy functional $\mathcal{F}$ is carried out by gradient descent method:

$$\frac{\partial \phi}{\partial t} = -\frac{\partial F_{2\_phase}}{\partial \phi}.$$

5. The computer implemented method of of claim 1, wherein the energy functional is:

$$\mathcal{F}_{multiphase}(\Phi,c,b) = (1-\lambda)\mathcal{E}_{region}(\Phi,c,b) + \lambda \mathcal{E}_{edge}(\Phi) + \mu \mathcal{R}_p(\Phi)$$

where $\lambda$ is greater than or equal to 0 and smaller than or equal to 1, $\mu$ is a positive constant, b is a bias field accounting for intensity inhomogeneity, c is a vector representing intensity-based constant values in disjoint regions, and $\phi$ is a vector formed by k level set functions $\phi i$, i=1 . . . k for k regions or phases;

$$\Phi = (\phi_1(y), \ldots, \phi_k(y))$$

and a number of the level set functions to be used is at least equal to:

$$k = \log_2(\mathcal{N})$$

where $\log_2$ is the logarithm to the base 2 and N is the number of the regions to be segmented in the image.

$$\mathcal{E}_{region}(\Phi,c,b) = \int \sum_{i=1}^{N} e_i(x) M_i(\Phi)x)) dx$$

With:

$$e_i(x) = \int K_\sigma |I(x)-b(y)c_i|^2 dy, \ i=1,\ldots,k$$

with $K_\sigma$, a kernel function computed by means of a truncated Gaussian function of standard deviation $\sigma$, referred to as the scale parameter, $\mathcal{M}_i$ is a membership function of each region $\Omega_i$, and is defined as:

$$M_i(\Phi) = M_i(\phi_1(y),\ldots,\phi_k(y)) = \begin{cases} 1, & y \in \Omega_i \\ 0, & \text{else} \end{cases}$$

$$\mathcal{E}_{edge}(\Phi) = v \mathcal{L}_g(\Phi) + \alpha \mathcal{A}_g(\Phi)$$

Where:

$$\mathcal{L}_g(\Phi) = \sum_{j=1}^{k} \mathcal{L}_g(\phi_j)$$

$$\mathcal{A}_g(\Phi) = \sum_{j=1}^{k} \mathcal{A}_g(\phi_j)$$

wherein $v$ and $\alpha$ are normalization constants,
wherein $\mathcal{R}_p$ is a regularisation term:

$$\mathcal{R}_p(\phi) = \int p(|\nabla \phi|) dx$$

and the minimization of the multiphase hybrid energy functional $\mathcal{F}_{multiphase}$ by gradient descent method:

$$\frac{\partial \phi_1}{\partial t} = -\frac{\partial Fmult_{iphase}(\Phi)}{\partial \phi_1}, \ldots, \frac{\partial \phi_k}{\partial t} = -\frac{\partial Fmu_{ltiphase}(\Phi)}{\partial \phi_k}.$$

6. A computer implemented method for performing bone segmentation in imaging data of at least a section of a body structure including a plurality of bones using anatomical knowledge data relative to the section of the body structure of the imaging data, the method comprising:
   Obtaining the imaging data including a plurality of 2D images of the section of the body structure;
   Generating primary image data from the imaging data using an image preprocessing including identifying regions of interest (ROIs) in the 2D images;
   Generating secondary segmented image data including a plurality of 2D binary images with segmented blobs by performing a multiphase local-based hybrid level set segmentation on the regions of interest (ROIs) by minimizing an energy functional including a local-based edge term and a local-based region term computed locally inside a local neighborhood centered at each point of a respective one of the regions of interest (ROIs), the local neighborhood being defined by a Gaussian kernel;
   Generating a 3D volume including a plurality of 3D subvolumes from the segmented blobs of the secondary segmented image data; and
   Associating an anatomical component to each one of the 3D subvolumes using the anatomical knowledge data relative to the section of the body structure of the imaging data.

7. The computer implemented method of claim 6, wherein the plurality of 2D images are greyscale images and the image preprocessing further comprises performing a 3D adaptive thresholding processing to define thresholded blobs in the 2D images and generating binary masks from the thresholded blobs obtained by the 3D adaptive thresholding processing, wherein the 3D adaptive thresholding processing includes the steps of:
   For at least a sample of the plurality of 2D greyscale images:
      Dividing each one of the 2D greyscale images of at least the sample in a plurality of sections;
      Computing a local pixel intensity section threshold for each one of the sections;
      Computing a global image pixel intensity threshold for each one of the 2D greyscale images of at least the sample using the local pixel intensity section thresholds computed for each one of the sections;
      Computing a global volume pixel intensity threshold using the global image pixel intensity thresholds; and
   Applying the global volume pixel intensity threshold to each one of the 2D greyscale images of the plurality of 2D greyscale images.

8. The computer implemented method of claim 7, wherein the global image pixel intensity threshold for each one of the 2D greyscale images of at least the sample is computed as a maximum of the local pixel intensity section thresholds for the corresponding image; and the global volume pixel intensity threshold from the global image pixel intensity thresholds is computed as a mean of the global image pixel intensity thresholds minus 1.5 times a standard deviation of the global image pixel intensity thresholds [mean(global image pixel intensity thresholds)−1.5std(global image pixel intensity thresholds)].

9. The computer implemented method of claim 7, wherein the image preprocessing comprises computing thresholded blobs in the images following the 3D adaptive thresholding processing and creating binary masks from the thresholded blobs; and wherein identifying regions of interest (ROIs) in the 2D images comprises selecting regions in the 2D greyscale images of the imaging data including at least one of the a respective one of the thresholded blobs and a respective one of the binary masks generated from the thresholded blobs.

10. The computer implemented method of claim 9, wherein generating secondary segmented image data comprises performing a blob masking validation following the multiphase local-based hybrid level set segmentation, the multiphase local-based hybrid level set segmentation generating a plurality of unmasked blobs, and wherein the blob masking validation comprises:
   Applying the binary masks to the unmasked blobs to obtain masked blobs;
   Determining at least one perceptual grouping property of each one of the masked blobs and the unmasked blobs;
   For each corresponding pair of masked blobs and unmasked blobs,
      Comparing the at least one perceptual grouping property of the masked blob to the at least one perceptual grouping property of the corresponding one of unmasked blobs; and
      Selecting the one of the masked blob and the corresponding one of unmasked blobs having the highest perceptual grouping property as the segmented blob of the secondary segmented image data.

11. The computer implemented method of claim 9, further comprising initializing the multiphase local-based hybrid level set segmentation with the binary masks.

12. The computer implemented method of claim 9, wherein performing the multiphase local-based hybrid level set segmentation on the regions of interest (ROIs) comprises generating binary subimages including the segmented blobs and the method further comprises merging the binary subimages to generate a respective one of the 2D binary images including the segmented blobs.

13. The computer implemented method of claim 6, wherein the image preprocessing further comprises:
Determining an initial image including at least one region of interest and determining a final image including at least one region of interest; and
Selecting a subset of 2D images including the initial image, the final image, and the images extending therebetween, wherein the primary image data consists of the subset of 2D images including the regions of interest (ROIs).

14. The computer implemented method of claim 6, wherein identifying anatomical components in the 3D volume comprises:
Computing at least one subvolume feature for each one of the 3D subvolumes;
For each one of the 3D subvolumes, carrying out a bone identification processing comprising:
Identifying a closest one of the bones and comparing the at least one subvolume feature to features of the anatomical knowledge data corresponding to the closest one of the bones;
If the at least one subvolume feature for the respective one of the 3D subvolumes substantially corresponds to the features of the anatomical knowledge data for the closest one of the bones, associating the respective one of the 3D subvolumes to the closest one of the bones;
Otherwise, applying a selective 3D bone separation to the respective one of the 3D subvolumes and generating new 3D subvolumes.

15. The computer implemented method of claim 14, wherein identifying anatomical components in the 3D volume further comprises:
Identifying a 3D anatomical point of interest within the 3D volume;
Identifying a 3D subvolume closest to the 3D anatomical point of interest; and
Performing sequentially the bone identification processing by proximity to a last one of associated 3D subvolumes, starting from the 3D subvolume closest to the 3D anatomical point of interest.

16. The computer implemented method of claim 14, wherein the 3D volume generated from the 2D binary images of the secondary segmented image data is a first 3D volume and the method further comprises:
Carrying out a 2D blob separation on the secondary segmented image data and generating a second 3D volume by stacking binary images obtained following the 2D blob separation; and
wherein identifying anatomical components is performed on the second 3D volume.

17. The computer implemented method of claim 16, wherein carrying out a 2D blob separation comprises:
For each one of the segmented blobs of the secondary segmented image data:
Creating straight segments from the contours of the respective one of the segmented blobs;
Identifying points of interest using the straight segments;
If there is at least one point of interest, identifying at least one bone attachment location close to the at least one point of interest; and separating the respective one of the segmented blobs by local morphological erosion along the at least one bone attachment location.

18. The computer implemented method of claim 17, wherein identifying points of interest using the straight segments comprises:
Determining a length of the straight segments and an angle between consecutive ones of the straight segments, the consecutive one of the straight segments sharing a common point;
For each pair of consecutive straight segments $(s_1, s_2)$, computing a relevance measure $(K_{relevance})$:

$$K_{relevance} = \frac{\beta(s_1, s_2) l(s_1) l(s_2)}{l(s_1) + l(s_2)}$$

wherein $\beta(s_1, s_2)$ is the angle between the consecutive straight segments $s_1$ and $s_2$;
$l(s_1)$ and $l(s_2)$ are lengths of the consecutive straight segments $s_1$ and $s_2$ respectively;
Comparing the computed relevance measure to a predetermined threshold; and
If the computed relevance measure meets the predetermined relevance threshold, identifying the common point as being a point of interest.

19. The computer implemented method of claim 18, wherein identifying at least one bone attachment location close to the at least one point of interest comprises:
Identifying if a respective one of the points of interest belongs to a linear bone attachment location defined by a pair of points of interest; and, for each identified linear bone attachment location, separating the respective one of the segmented blobs comprises performing a linear local morphological erosion along a line extending between the points of interest defining the linear bone attachment location;
otherwise, identifying the respective one of the points of interest as a punctual bone attachment location and separating the respective one of the segmented blobs comprises performing local morphological erosion around the punctual bone attachment location.

20. The computer implemented method of claim 19, wherein identifying a pair of points of interest comprises: for each potential pair of points of interest, grouping the points of interest in a pair and computing a distance separating two grouped points of the pair, comparing the computed distance to a predetermined distance threshold; and if the computed distance meets the predetermined distance threshold, associating the potential pair of interest points as being one linear bone attachment location.

21. The computer implemented method of claim 6, wherein the local neighborhood is circular and performing the multiphase local-based hybrid level set segmentation further comprises: for each pixel of the regions of interest (ROIs), dynamically changing region descriptors based on a position of a center of the local neighborhood.

22. The computer implemented method of claim 6, further comprising: selecting a value λ of to adjust the performance of the multiphase local-based hybrid level set segmentation with λ being greater than 0 and smaller than 1, wherein λ multiplies the local-based edge term and (1−λ) multiplies local-based region term.

23. A system for generating segmentation data segmentation from imaging data of at least a section of a body structure including a plurality of bones using anatomical knowledge data relative to the section of the body structure of the imaging data, the system comprising:

a processing unit having a processor and a memory;

an image preprocessing module stored on the memory and executable by the processor, the image preprocessing module having program code that when executed, generates primary image data from the imaging data using an image preprocessing process, the primary image data including regions of interest in images of the imaging data;

a multi-bone segmentation module stored on the memory and executable by the processor, the multi-bone segmentation module having a program code that when executed, generates a 3D volume by performing a multiphase local-based hybrid level set segmentation to obtain a plurality of segmented blobs and combining the segmented blobs to obtain the 3D volume including a plurality of 3D subvolumes, the multiphase local-based hybrid level set segmentation being carried out on each one of on the regions of interest (ROIs) by minimizing an energy functional including a local-based edge term and a local-based region term computed locally inside a local neighborhood centered at each point of a respective one of the regions of interest (ROIs), the local neighborhood being defined by a Gaussian kernel and generating a 3D volume following the multiphase local-based hybrid level set segmentation; and an anatomical component identification module stored on the memory and executable by the processor, the anatomical component identification module having a program code that, when executed, generates tertiary segmented imaging data through identification of the subvolumes defined in the 3D volume and identification of bones defined by the subvolumes.

* * * * *

UNITED STATES PATENT AND TRADEMARK OFFICE
CERTIFICATE OF CORRECTION

PATENT NO. : 9,801,601 B2  
APPLICATION NO. : 14/982029  
DATED : October 31, 2017  
INVENTOR(S) : Rivet-Sabourin Geoffroy et al.

Page 1 of 2

It is certified that error appears in the above-identified patent and that said Letters Patent is hereby corrected as shown below:

On the Title Page

At item (72), Line 3, "Quebec (CA)" should be -- Québec (CA) --.

In the Claims

At Column 41, Line 21, "processor," should be -- processor; --.

At Column 41, Line 23, "structure; and" should be -- structure; --.

At Column 41, Line 53, "of of" should be -- of --.

At Column 42, Line 49, "of of" should be -- of --.

At Column 42, Line 67, "image." should be -- image, --.

At Column 43, Lines 32-33, " $\frac{\partial \phi_1}{\partial t} = -\frac{\partial F mult_{iphase}(\Phi)}{\partial \phi_1}, \ldots, \frac{\partial \phi_k}{\partial t} = -\frac{\partial F mu_{ltiphase}(\Phi)}{\partial \phi_k}.$ "

should be -- $\frac{\partial \phi_1}{\partial t} = -\frac{\partial F_{multiphase}(\Phi)}{\partial \phi_1}, \ldots, \frac{\partial \phi_k}{\partial t} = -\frac{\partial F_{multiphase}(\Phi)}{\partial \phi_k}.$ --.

At Column 44, Lines 37-38, "the a" should be -- a --.

At Column 46, Line 21, "I(s₁) and I(s₂)" should be -- l(s₁) and l(s₂) --.

Signed and Sealed this  
Twenty-eighth Day of May, 2019

Andrei Iancu  
*Director of the United States Patent and Trademark Office*

CERTIFICATE OF CORRECTION (continued)
U.S. Pat. No. 9,801,601 B2

At Column 46, Line 60, "value $\lambda$ of" should be -- value of $\lambda$ --.

At Column 46, Lines 65-66, "segmentation data segmentation" should be -- segmentation data --.

At Column 48, Line 2, "of on the" should be -- of the --.